(12) United States Patent
Schmidt et al.

(10) Patent No.: US 6,664,078 B1
(45) Date of Patent: Dec. 16, 2003

(54) METHOD FOR THE ISOLATION OF CCC PLASMID DNA

(75) Inventors: Torsten Schmidt, Lage (DE); Karl Friehs, Sehnde (DE); Erwin Flaschel, Bielefeld (DE); Martin Schleef, Bielefeld (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 09/700,934

(22) PCT Filed: May 21, 1999

(86) PCT No.: PCT/EP99/03522

§ 371 (c)(1),
(2), (4) Date: Nov. 21, 2000

(87) PCT Pub. No.: WO99/61633

PCT Pub. Date: Dec. 2, 1999

(30) Foreign Application Priority Data

May 25, 1998 (EP) .............................. 98109473

(51) Int. Cl.[7] .......................... C12P 19/34; C12N 1/00; C12N 1/20
(52) U.S. Cl. ..................... 435/91.1; 435/89; 435/252.8; 435/259; 435/243
(58) Field of Search ...................... 435/91.1, 89, 252.8, 435/259, 243

(56) References Cited

U.S. PATENT DOCUMENTS 5,955,323 A    9/1999   Chen

FOREIGN PATENT DOCUMENTS

| DD | 239 222 A1 | 9/1986 |
|---|---|---|
| DD | 299 380 A7 | 4/1992 |
| WO | WO 96/40905 A | 12/1996 |

OTHER PUBLICATIONS

English language translation of German patent document 299380 A7.*
English language translation of German patent document 239222 A1.*
Chen et al. Journal of Industrial Microbiology and Biotechnology 18:43–48 1997.*
Chen et al., *Journal of Industrial Microbiology & Biotechnology* 18:43–45 (1997).
Korz et al., *Journal of Biotechnology* 39: 59–65 (1995).
Lahijani et al., *Human Gene Therapy* 7: 1971–1980 (1996).
Lee et al., *Trends in Biotechnology* 14: 99–105 (1996).
Prazeres et al., *Trends in Biotechnology* 17: 169–174 (1999).
Schleef et al., *Journal of Molecular Medicine* 76: B61 (1998).

* cited by examiner

*Primary Examiner*—David Guzo
*Assistant Examiner*—David A. Lambertson
(74) *Attorney, Agent, or Firm*—Yankwich & Associates; Leon R. Yankwich; Michael R. Wesolowski

(57) ABSTRACT

The present invention relates to the production of biomass for the isolation of ccc plasmid DNA comprising culturing a bacterial transformant in a bioreactor containing an antibiotic-free batch medium under batch-conditions and, at the end of the batch phase, feeding under feed-back conditions the portion of a feed-back medium after the rise of the concentration of dissolved oxigen above a threshold-set point. Said feed-back medium comprises besides a carbon source a magnesium salt, preferably in concentrations above 20 mM. Preferably, the bacterial transformant is harvested after the end of the culture and frozen or freeze-dried. Also preferred is that ccc plasmid DNA is, optionally directly, isolated after harvesting the bacteria.

31 Claims, 21 Drawing Sheets

Figure 1:
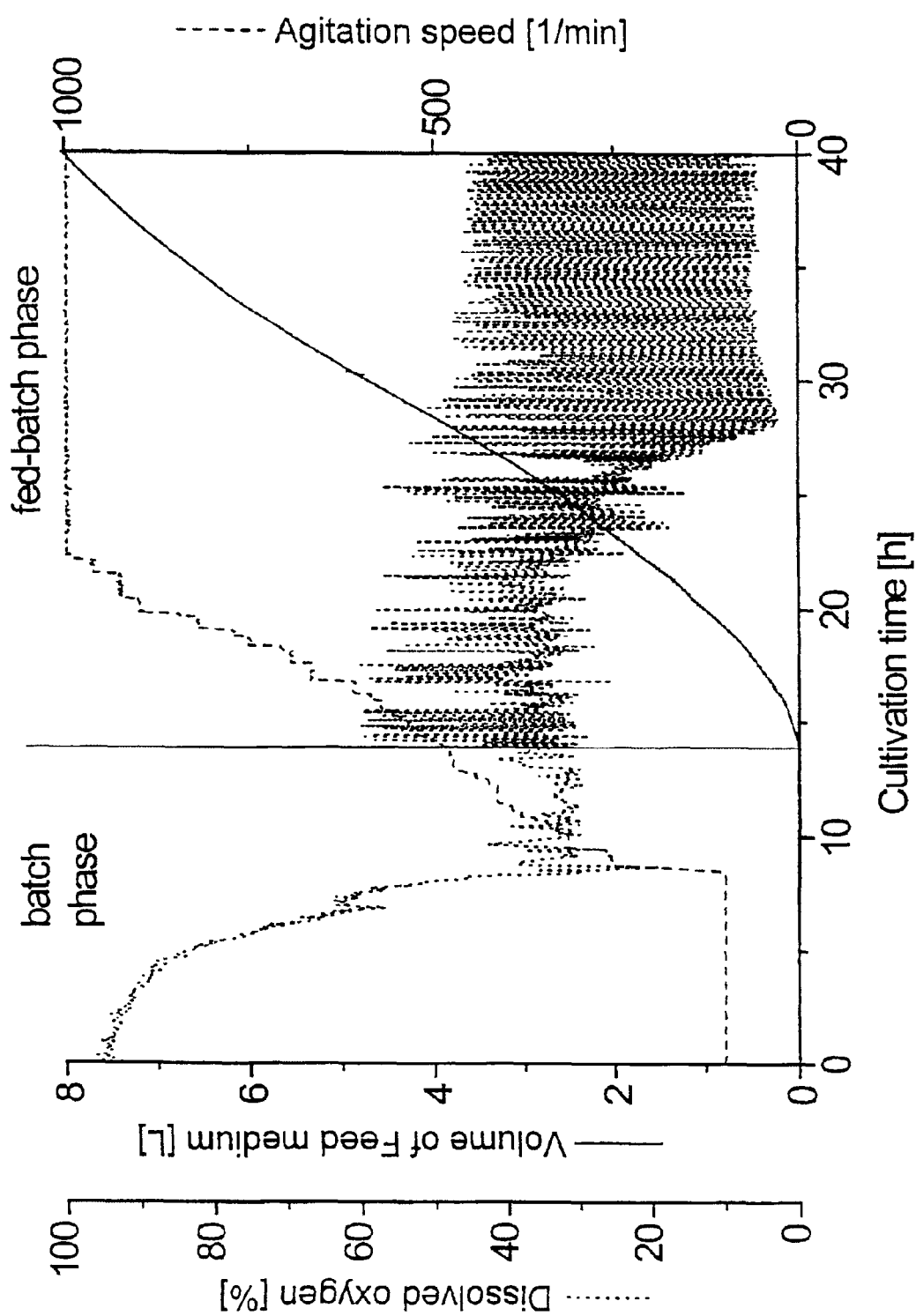

The 4,5 kbp EcoRI-HindIII-restriction fragment of pCMVβ (Clontech Laboratories; , Palo Alto, California, USA), containing the β-galactosidase gene under the control of the CMV-promoter, was cloned into the corresponding restriction sites of pUK21 (Vieira, J., and Messing, J., 1991, Gene 100:189-194).

Fig. 11 pUK21-CMVβ

```
             10         20         30         40         50         60
     1  AAGCTTGCAT GCCTGCAGGT CGACTCTAGA GGATCCGAAA AAACCTCCCA CACCTCCCCC   60
    61  TGAACCTGAA ACATAAAATG AATGCAATTG TTGTTGTTAA CTTGTTTATT GCAGCTTATA  120
   121  ATGGTTACAA ATAAAGCAAT AGCATCACAA ATTTCACAAA TAAAGCATTT TTTTCACTGC  180
   181  ATTCTAGTTG TGGTTTGTCC AAACTCATCA ATGTATCTTA TCATGTCTGG ATCCCCGCGG  240
   241  CCGCCTAGAG TCGAGGCCGA GTTTGTCAGA AAGCAGACCA AACAGCGGTT GGAATAATAG  300
   301  CGAGAACAGA GAAATAGCGG CAAAAATAAT ACCCGTATCA CTTTTGCTGA TATGGTTGAT  360
   361  GTCATGTAGC CAAATCGGGA GTAGGCTCCC ATGATAAAAA AGTAAAAGAA  420
   421  AAAGAATAAA CCGAACATCC AAAAGTTTGT GTTTTTTAAA TAGTACATAA TGGATTTCCT  480
   481  TACGCGAAAT ACGGGCAGAC ATGGCCTGCC CGGTTATTAT TATTTTTGAC ACCAGACCAA  540
   541  CTGGTAATGG TAGCGACCGG CGCTCAGCTG GAATTCCGCC GATACTGACG GGCTCCAGGA  600
   601  GTCGTCGCCA CCAATCCCCA TATGGAAACC GTCGATATTC AGCCATGTGC CTTCTTCCGC  660
   661  GTCCAGCAGA TGGCCGATGG CTGTTTCCAT CAGTTGCTGT TGACTGTAGC GGCTGATGTT  720
   721  GAACTGGAAG TCGCCGCGCC ACTGGTGTGG GCCATAATTC AATTCGCGCG TCCCGCAGCG  780
   781  CAGACCGTTT TCGCTCGGGA AGACGTACGG GGTATACATG TCTGACAATG GCAGATCCCA  840
   841  GCGGTCAAAA CAGGCGGCAG TAAGGCGGTC GGGATAGTTT TCTTGCGGCC CTAATCCGAG  900
   901  CCAGTTTACC CGCTCTGCTA CCTGCGCCAG CTGGCAGTTC AGGCCAATCC ATTTGACCAC  960
   961  CGGGTATCG CTCGCCACTT CAACATCAAC GGTAATAAGGT TTTCCCCTGA TGCTGCCACG CGTGAGCGGT 1020
  1021  CGGTGTATC TTCCGGCTGA TAAATAAGGT ATTTGACCGA TGCTGCCACG CGTGAGCGGT 1080
  1081  CGTAATCAGC ACCGCATCAG CAAGTGTATC CAAGTGTATC TGCAACAACG CTGCTTCGGC 1140
```

Fig. 11 cont.

```
1141 CTGGTAATGG CCCGCCGCCT TCCAGCGTTC GACCCAGCCG TTAGGGTCAA TGCGGGTCGC 1200
1201 TTCACTTACG CCAATGTCGT TATCCAGCGG TGCACGGGTG AACTGATCGC GCAGCGCGT  1260
1261 CAGCAGTTGT TTTTTATCGC CAATCCACAT CTGTGAAAGA AAGCCTGACT GGCGGTTAAA 1320
1321 TTGCCAACGC TTATTACCCA GCTCGATGCA AAATCCATT  TCGCTGGTGG TCAGATGCGG 1380
1381 GATGGCGTGG GACGCGGCGG GGAGCGTCAC ACTGAGGTTT TCCGCCAGAC GCCACTGCTG 1440
1441 CCAGGCGCTG ATGTGCCCGG CTTCTGACCA TGCGGTCGCG TTCGGTTGCA CTACGCGTAC 1500
1501 TGTGAGCCAG AGTTGCCCGG CGCTCTCCGG CTGCGGTAGT TCAGGCAGTT CAATCAACTG 1560
1561 TTTACCTTGT GGAGCGACAT CCAGAGGCAC TTCACCGCTT GCCAGCGCGT TACCATCCAG 1620
1621 CGCCACCATC CAGTGCAGGA GCTCGTTATC GCTATGACGG AACAGGTATT CGCTGGTCAC 1680
1681 TTCGATGGTT TGCCCGGATA AACGGAACTG GAAAAACTGC TGCTGGTGTT TTGCTTCCGT 1740
1741 CAGGCGCTGA TGCGGCGTGC GGTCGGCAAA GACCAGACCG TTCATACAGA ACTGGCGATC 1800
1801 GTTCGGCGTA TCGCCAAAAT CACCGCCGTA AGCCGACCAC GGGTTGCCGT TTTCATCATA 1860
1861 TTTAATCAGC GACTGATCCA CCCAGTCCCA GACGAAGCCG CCCTGTAAAC GGGGATACTG 1920
1921 ACGAAACGCC TGCCAGTATT TAGCGAACC  GCCAAGACTG TTACCCATCG CGTGGGCGTA 1980
1981 TTCGCAAAGG ATCAGCGGGC GGCTCTCTCC AGTAGCCGAA AGCCATTTTT TGATGGACCA 2040
2041 TTTCGGCACA GCCGGAAGG  GCTGGTCTTC ATCCACGCGC GCGTACATCG GGCAAATAAT 2100
2101 ATCGGTGGCC GTGGTGTCGG CTCCGCCGCC TTCATACTGC ACCGGGGCGGG AAGGATCGAC 2160
2161 AGATTTGATC CAGCGATACA GCGGGTCGTG ATTAGCGCCG TGGCCTGATT CATTCCCCAG 2220
2221 CGACCAGATG CAGGATATCG GGTGATTACG ATCGCGCTGC ACCATTCGCG TTACGCGTTC 2280
2281 GCTCATCGCC GGTAGCCAGC GCGGATCATC GGTCAGACGA TTCATTGGCA CCATGCCGTG 2340
2341 GGTTTCAATA TTGGCTTCAT CCACCACATA CAGGCCGTAG CGGTCGCACA GCGTGTACCA 2400
2401 CAGCGGATGG TTCGGATAAT GCGAACAGCG CACGGCGGTTA AAGTTGTTCT GCTTCATCAG 2460
2461 CAGGATATCC TGCACCATCG TCTGCTCATC CATGACCTGA CCATGCAGAG GATGATGCTC 2520
2521 GTGACGGTTA ACGCCTCGAA TCAGCAACGG CTTGCCGTTC AGCAGCAGCA GACCATTTC  2580
2581 AATCCGCACC TCGCGGAAAC CGACATGCA  GGCTTCTGCT TCAATCAGCG TGCCGTCGGC 2640
2641 GGTGTGCAGT TCAACCACCG CACGATAGAG CACGATAGAG CACGATAGAG ACAGTTTCGG 2700
```

Fig. 11 cont.

```
2701 GTTTTCGACG TTCAGACGTA GTGTGACGCG ATCGGCATAA CCACCACGCT CATCGATAAT 2760
2761 TTCACCGCCG AAAGGCGCGG TGCCGCTGGC GACCTGCGTT TCACCCTGCC ATAAAGAAAC 2820
2821 TGTTACCCGT AGGTAGTCAC GCAACTCGCC GCACATCTGA ACTTCAGCCT CCAGTACAGC 2880
2881 GCGGCTGAAA TCATCATTAA AGCGAGTGGC AACATGGAAA TCGCTGATTT GTGTAGTCGG 2940
2941 TTTATGCAGC AACGAGACGT CACGGAGTGT GCCGCTCATC CGCCACATAT CCTGATCTTC 3000
3001 CAGATAACTG CCGTCACTCC AACGCAGCAC CATCACCGCG AGGCGGTTTT CTCCGGCGCG 3060
3061 TAAAAATGCG CTCAGTCAA ATTCAGACGG CAAACGACTG TCCTGGCCGT AACCGACCCA 3120
3121 GCGCCCGTTG CACCACAGAT GAAACGCCGA GTTAACGCCA TCAAAAATAA TTCGCGTCTG 3180
3181 GCCTTCCTGT AGCCAGCTTT CATCAACATT AAATGTGAGC GAGTAACAAC CCGTCGGATT 3240
3241 CTCCGTGGGA ACAAACGGGG GATTGACCGT AATGGATATAG GTTACGTTGG TGTAGATGGG 3300
3301 CGCATCGTAA CCGTGCATCT GCCAGTTTGA GGGGACGACG ACAGTATCGG CCTCAGGAAG 3360
3361 ATCGCACTCC AGCCAGCTTT CCGGCACCGC TTCTGGTGCC GGAAACCAGG CAAAGCGCCA 3420
3421 TTCGCCATTC AGGCTGCGCA ACTGTTGGGA AGGGCGATCG GTGCGGGCCT CTTCGCTATT 3480
3481 ACGCCAGCTG GCGAAAGGGG GATGTGCTGC AAGGCGATTA AGTTGGGTAA CGCCAGGGTT 3540
3541 TTCCCAGTCA CGACGTTGTA AAACGACGGG ATCGCGCTTG AGCAGCTCCT TGCTGGTGTC 3600
3601 CAGACCAATG CCTCCCAGAC CGGCAACGAA AATCACGTTC TTGTTGGTCA AAGTAAACGA 3660
3661 CATGGTGACT TCTTTTTTGC TTTAGCAGGC TCTTTCGATC CCGGGAATT GCGGCCGCGG 3720
3721 GTACAATTCC GCAGCTTTTA GAGGAGCAG AACACTTCCG TACAGGCCTA GAAGTAAAGG 3780
3781 CAACATCCAC TGAGGAGCAG TTCTTTGATT TGCACCACCA CCGGATCCGG GACCTGAAAT 3840
3841 AAAAGACAAA AAGACTAAAC TTACCAGTTA ACTTTCTGGT TTTTCAGTTC CTCGAGTACC 3900
3901 GGATCCTCTA GAGTCCCGGA AAGACTAAAC TCCCGGGTGT TTCTATGAG GTCAAAACAG 3960
3961 CGTGGATGGC GTCTCCAGGC GATCTGACGG TTCACTAAAC GAGCTCTGCT TATATAGACC 4020
4021 TCCCACCGTA CACGGCCTACC GCCCATTTGC GTCAATGGGG CGGAGTTGTT ACGACATTTT 4080
4081 GGAAAGTCCC GTTGATTTTG GTGCCAAAAC AAACTCCCAT TGACGTCAAT GGGTGAGA 4140
4141 CTTGGAAATC CCCGTGAGTC AAACCGCTAT CCACGCCCAT TGATGTACTG CCAAACCGC 4200
4201 ATCACCATGG TAATAGCGAT GACTAATACG TAGATGTACT GCCAAGTAGG AAAGTCCCAT 4260
```

Fig. 11 cont.

| | | | | |
|---|---|---|---|---|
| 4261 | AAGGTCATGT | ACTGGGCATA | ATGCCAGGCG | GGCCATTTAC | CGTCATTGAC | GTCAATAGGG | 4320 |
| 4321 | GGCGTACTTG | GCATATGATA | CACTTGATGT | ACTGCCAAGT | GGGCAGTTTA | CCGTAAATAC | 4380 |
| 4381 | TCCACCCATT | GACGTCAATG | GAAAGTCCCT | ATTGGCGTTA | CTATGGGAAC | ATACGTCATT | 4440 |
| 4441 | ATTGACGTCA | ATGGGCGGGG | GTCGTTGGGC | GGTCAGCCAG | GCGGGCCATT | TACCGTAAGT | 4500 |
| 4501 | TATGTAACGA | CCTGCAGGCA | TGCAAGCTCG | AATTCGAGCT | CCCGGGTACC | ATGGCATGCA | 4560 |
| 4561 | TCGATAGATC | TCGAGGCCTC | GGACTAGTGG | CGTAATCATG | GTCATAGCTG | TTTCCTGTGT | 4620 |
| 4621 | GAAATTGTTA | TCCGCTCACA | ATTCCACACA | ACATACGAGC | CGCGAAGCA | TAAAGTGTAA | 4680 |
| 4681 | AGCCTGGGGT | GCCTAATGAG | TGAGCTAACT | CACATTAATT | GCGTTGCGCT | CACTGCCCGC | 4740 |
| 4741 | TTTCCAGTCG | GGAAACCTGT | CGTGCCAGCT | GCATTAATGA | ATCGGCCAAC | GCGCGGGGAG | 4800 |
| 4801 | AGGCGGTTTG | CGTATTGGGC | GCTCTTCCGC | TTCCTCGCTC | ACTGACTCGC | TGCGCTCGT | 4860 |
| 4861 | CGTTCGGCTG | CGGCGAGCGG | TATCAGCTCA | CTCAAAGGCG | GTAATACGGT | TATCCACAGA | 4920 |
| 4921 | ATCAGGGGAT | AACGCAGGAA | AGAACATGTG | AGCAAAAGGC | CAGCAAAAGG | CCAGGAACCG | 4980 |
| 4981 | TAAAAAGGCC | GCGTTGCTGG | CGTTTTTCCA | TAGGCTCCGC | CCCCCTGACG | AGCATCACAA | 5040 |
| 5041 | AAATCGACGC | TCAAGTCAGA | GGTGGCGAAA | CCCGACAGGA | CTATAAAGAT | ACCAGGCGTT | 5100 |
| 5101 | TCCCCCTGGA | AGCTCCCTCG | TGCGCTCTCC | TGTTCCGACC | CTGCCGCTTA | CCGGATACCT | 5160 |
| 5161 | GTCCGCCTTT | CTCCCTTCGG | GAAGCGTGGC | GCTTTCTCAT | AGCTCACGCT | GTAGGTATCT | 5220 |
| 5221 | CAGTTCGGTG | TAGGTCGTTC | GCTCCAAGCT | GGGCTGTGTG | CACGAACCCC | CCGTTCAGCC | 5280 |
| 5281 | CGACCGCTGC | GCCTTATCCG | GTAACTATCG | TCTTGAGTCC | AACCCGGTAA | GACACGACTT | 5340 |
| 5341 | ATCGCCACTG | GCAGCAGCCA | CTGGTAACAG | GATTAGCAGA | GCGAGGTATG | TAGGCGGTGC | 5400 |
| 5401 | TACAGAGTTC | TTGAAGTGGT | GGCCTAACTA | CGGCTACACT | AGAAGAACAG | TATTTGGTAT | 5460 |
| 5461 | CTGCGCTCTG | CTGAAGCCAG | TTACCTTCGG | AAAAAGAGTT | GGTAGCTCTT | GATCCGGCAA | 5520 |
| 5521 | ACAAACCACC | GCTGGTAGCG | GTGGTTTTTT | TGTTTGCAAG | CAGCAGATTA | CGCGCAGAAA | 5580 |
| 5581 | AAAAGGATCT | CAAGAAGATC | CTTTGATCTT | TTCTACGGGG | TCTGACGCTC | AGTGGAACGA | 5640 |
| 5641 | AAACTCACGT | TAAGGGATTT | TGGTCATGAG | ATTATCAAAA | AGGATCTTCA | CCTAGATCCT | 5700 |
| 5641 | AAACTCACGT | TAAGGGATTT | TGGTCATGAG | CTTGCGCCGT | CCCGTCAAGT | CAGCGTAATG | 5700 |
| 5701 | CTCTGCCAGT | GTTACAACCA | ATTAACCAAT | TCTGATTAGA | AAAACTCATC | GAGCATCAAA | 5760 |
| 5761 | TGAAACTGCA | ATTTATTCAT | ATCAGGATTA | TCAATACCAT | ATTTTTGAAA | AAGCCGTTTC | 5820 |

Fig. 11 cont.

| | | | | | |
|---|---|---|---|---|---|
| 5821 | TGTAATGAAG | GAGAAAACTC | ACCGAGGCAG | TTCCATAGGA | TGGCAAGATC | CTGGTATCGG | 5880 |
| 5881 | TCTGCGATTC | CGACTCGTCC | AACATCAATA | CAACCTATTA | ATTCCCCTC | GTCAAAAATA | 5940 |
| 5941 | AGGTTATCAA | GTGAGAAATC | ACCATGAGTG | ACGACTGAAT | CCGGTGAGAA | TGGCAAAAGT | 6000 |
| 6001 | TTATGCATTT | CTTTCCAGAC | TTGTTCAACA | GGCCAGCCAT | TACGCTCGTC | ATCAAAATCA | 6060 |
| 6061 | CTCGCATCAA | CCAAACCGTT | ATTCATTCGT | GATTGCGCCT | GAGCGAGACG | AAATACGCGA | 6120 |
| 6121 | TCGCTGTTAA | AAGGACAATT | ACAAACAGGA | ATCGAATGCA | ACCGGCGCAG | GAACACTGCC | 6180 |
| 6181 | AGCGCATCAA | CAATATTTTC | ACCTGAATCA | GGATATTCTT | CTAATACCTG | GAATGCTGTT | 6240 |
| 6241 | TTTCCGGGGA | TCGCAGTGGT | GAGTAACCAT | GCATCATCAG | GAGTACGGAT | AAAATGCTTG | 6300 |
| 6301 | ATGGTCGAA | GAGGCATAAA | TTCCGTCAGC | CAGTTTAGTC | TGACCATCTC | ATCTGTAACA | 6360 |
| 6361 | TCATTGGCAA | CGCTACCTTT | GCCATGTTTC | AGAAACAACT | CTGGGCGCATC | GGGCTTCCCA | 6420 |
| 6421 | TACAAGCGAT | AGATTGTCGC | ACCTGATTGC | CGGACATTAT | CGCGAGCCCA | TTTATACCCA | 6480 |
| 6481 | TATAAATCAG | CATCCATGTT | GGAATTTAAT | ACTGTTTATG | ACGTTTCCCG | TTGAATATGG | 6540 |
| 6541 | CTCATAAACAC | CCCTTGTATT | ACTGTTTATT | GTAACATCAG | TAAGCAGACA | TCATGATGAT | 6600 |
| 6601 | ATATTTTAT | CTGTGCAAT | GTAACAAAATA | AGATTTTGAG | ACACAACGTG | GCTTTCCCCC | 6660 |
| 6661 | CCCCCCCAT | GACATTAACC | TATAAAAATA | GGCGTATCAC | GAGGCCCTTT | CGTCTCGCGC | 6720 |
| 6721 | GTTTCGGGTGA | TGACGGTGAA | AACCTCTGAC | ACATGCAGCT | CCCGGAGACG | GTCACAGCTT | 6780 |
| 6781 | GTCTGTAAGC | GGATGCCGGG | AGCAGACAAG | CCCGTCAGG | CGCGTCAGCG | GGTGTTGGCG | 6840 |
| 6841 | GGTGTCGGGG | CTGGCTTAAC | TATGCGGCAT | CAGAGCAGAT | TGTACTGAGA | GTGCACCATA | 6900 |
| 6901 | AAATTGTAAA | CGTTAATATT | TTGTTAAAAT | TCGCGTTAAA | TTTTTGTTAA | ATCAGCTCAT | 6960 |
| 6961 | TTTTTAACCA | ATAGACCGAA | ATCGGCAAAA | TCCCTTATAA | ATCAAAAGAA | TAGCCCGAGA | 7020 |
| 7021 | TAGAGTTGAG | TGTTGTTCCA | GTTTGGAACA | AGAGTCCACT | ATTAAAGAAC | GTGGACTCCA | 7080 |
| 7081 | ACGTCAAAGG | GCGAAAAACC | GTCTATCAGG | GCGATGGCCC | ACCCGATTT | AGAGCTTGAC | 7140 |
| 7141 | GGGGAAAGCC | GGCGAACGTG | GCGAGAAAGG | AAGGGAAGAA | AGCGAAAGGA | GCGGGCGCTA | 7200 |
| 7201 | AGCGGCTGC | AAGTGTAGCG | GTCACGCTGC | GCGTAACCAC | CACACCCGCC | GCGCTTAATG | 7260 |
| 7261 | CGCCGCTACA | GGGCGCGTAC | TATGGTTGCT | TGACGTATG | CGGTGTGAAA | TACCGCACAG | 7320 |
| 7321 | ATGCGTAAGG | AGAAAATACC | GCATCAGGCG | CCATTCGCCA | TTCAGGCTGC | GCAACTGTTG | 7380 |

Fig. 11 cont.

```
7381 GGAAGGGCGA TCGGTGCGGG CCTCTTCGCT ATTACGCCAG CTGGCGAAAG GGGGATGTGC 7440
7441 TGCAAGGCGA TTAAGTTGGG TAACGCCAGG GTTTCCCAG TCACGACGTT GTAAAACGAC 7500
7501 GGCCAGTGAA TTGTAATACG ACTCACTATA GGGCGAATTG GGATCGATC CACTAGTTCT 7560
7561 AGAGCGGCCG CCACGGGCGAT ATCGGATCCA TATGACGTCG ACGCGTCTGC AG       7612
              |         |         |         |         |         |
             10        20        30        40        50        60
```

Fig. 13

```
pUT649
           10         20         30         40         50         60
      |         |         |         |         |         |         |
   1  CATATGGTGA CCCGGATCCAC GCGTTCGAAC TAGTTAACTA GATCTAGAGT CCGTTACATA    60
  61  ACTTACGGTA AATGGCCCGC CTGGCTGACC GCCCAACGAC CCCCGCCCAT TGACGTCAAT   120
 121  AATGACGTAT GTTCCCATAG TAAACGCCAA AGGGACTTTC CATTGACGTC AATGGGTGGA   180
 181  GTATTTACGG TAAACTGCCC ACTTGGCAGT ACATCAAGTG TATCATATGC CAAGTACGCC   240
 241  CCCTATTGAC GTCAATGACG GTAAATGGCC CGCCTGGCAT TATGCCCAGT ACATGACCTT   300
 301  ATGGGACTTT CCTACTTGGC AGTACATCTA CGTATTAGTC ATCGCTATTA CCATGGTGAT   360
 361  GCGGTTTTGG CAGTACATCA ATGGGCGTGG ATAGCGGTTT GACTCACGGG GATTTCCAAG   420
 421  TCTCCACCCC ATTGACGTCA ATGGGAGTTT GTTTTGGCAC CAAAATCAAC GGGACTTTCC   480
 481  AAAAGTCGT AACAACTCCG CCCCATTGAC GCAAATGGGC GGTAGGCGTG TACGGTGGGA    540
 541  GGTCTATATA AGCAGAGCTC GTTTAGTGAA CCGTCAGATC GCCTGGAGAC GCCATCCACG   600
 601  CTGTTTTGAC CTCCATAGAA GACACCGGGA CCGATCCAGC CTCCGCGGCC GGGAACGGTG   660
 661  CATTGGAACG CGGCTGCAGC ACGTGTTGAC AATTAATCAT CGGTCACTAT TATCGGCATA   720
 721  GTATAATACG ACTCACTATA GGAGGCCAC CATGGCCCTG TACCCCGCC ATCAACACGC    780
 781  GTCTGCGTTC GACCAGGCTG CGCGTTCTCG CGGCCATAGC AACCGACGTA CGGCGTTGCG   840
 841  CCCTCGCCGG CAGCAAGAAG CCACGGAAGT CGGCCCCGGAG CCGCCCATGC CCACGCTACT   900
 901  GCGGGTTTAT ATAGACGGTC CCCACGGGAT GGGGAAAACC CAGAAAATGC AACTGCTGGT   960
 961  GGCCCTGGGT TCGCGCGACG ATATCGTCTA CGTACCCGAG ACCACCACGC CCGATGACTT  1020
1021  GCTGGGGCT TCCGAGACAA TCGCGAACAT CTACACCACA CAACACCGCC TCGACCAGGG  1080
1081  TGAGATATCG GCCGGGGACG GGCGGGTGGT AATGACAAGC GCCCAGATAA CAATGGGCAT  1140
```

Fig. 13 cont.

```
1141  GCCTTATGCC  GTGACCGACG  CCGTTCTGGC  TCCTCATATC  GGGGGGGAGG  CTGGGAGCTC  1200
1201  ACATGCCCCG  CCCCCGGCCC  TCACCCTCAT  CTTCGACCGC  CATCCCATCG  CCGCCCTCCT  1260
1261  GTGCTACCCG  GCCGCGCGGT  ACCTTATGGG  CAGCATGACC  CCCAGGCCG   TGCTGGCGTT  1320
1321  CGTGGCCCTC  ATCCCGCCGA  CCTTGCCCGG  CACCAACATC  GTGCTTGGGG  CCCTTCCGGA  1380
1381  GGACAGACAC  ATCGACCGCC  TGGCCAAACG  CCAGCGCCCC  GGCGAGCGGC  TGGACCTGGC  1440
1441  TATGCTGGCT  GCGATTCGCC  GCGTTTACGG  GCTACTTGCC  AATACGGTGC  GGTATCTGCA  1500
1501  GTGCGGCGGG  TCGTGGGCGG  AGGACTGGGG  ACAGCTTTCG  GGGACGGCCG  TGCCGCCCCA  1560
1561  GGGTGCCGAC  CCCCAGAGCA  ACGCGGGCCC  ACGACCCCAT  ATCGGGGACA  CGTTATTTAC  1620
1621  CCTGTTTCGG  GCCCCCGAGT  TGCTGGCCCC  CAACGGCGAC  CTGTATAACG  TGTTTGCCTG  1680
1681  GGCCTTGGAC  GTCTTGGCCA  AACGCCTCCG  TTCCATGCAC  GTCTTTATCC  TGGATTACGA  1740
1741  CCAATCGCCC  GCCGGCTGCC  GGGACGCCCT  GCTGCAACTT  ACCTCCGGGA  TGGTCCAGAC  1800
1801  CCACGTCACC  ACCCCGGCT   CCATACCGAC  GATATGCGAC  CTGGCCGCCA  CGTTTGCCCG  1860
1861  TGAGATGATC  AGCGGAGCTA  ATGGCGTCAT  GGCCAAGTTG  ACCAGTGCCG  TTCCGGTGCT  1920
1921  CACCGCGCGC  GACGTCGCCG  GAGCGGTCGA  GTTCTGGACC  GACCGGCTCG  GGTTCTCCCG  1980
1981  GGACTTCGTG  GAGGACGACT  TCGCCGGTGT  GGTCCGGGAC  GACGTGACCC  TGTTCATCAG  2040
2041  CGCGGTCCAG  GACCAGGTGG  TGCCGGACAA  CACCCTGGCC  TGGGTGTGGG  TGCGGGCCT   2100
2101  GGACGAGCTG  TACGCCGAGT  GGTCGGAGGT  CGTGTCCACG  AACTTCCGGG  ACGCCTCCGG  2160
2161  GCCGGCCATG  ACCGAGATCG  GCGAGCAGCC  GTGGGGGCGG  GAGTTCGCCC  TGCGCGACCC  2220
2221  GGCCGGCAAC  TGGCTGCACT  TCGTGGCCGA  GGAGCAGGAC  TGACCGACGC  CGACCAACAC  2280
2281  CGCCGGTCCG  ACGGCGGCCC  ACGGGTCCCA  GGGGGGTCGA  CCTCGAAAACT  TGTTTATTGC  2340
2341  AGCTTATAAT  GGTTACAAAT  AAAGCAATAG  CATCACAAAT  TTCACACAAAT  AAGCATTTTT  2400
2401  TTCACTGCAT  TCTAGTTGTG  GTTTGTCCAA  ACTCATCAAT  GTATCTTATC  ATGTCTGGAT  2460
2461  CCCTCGGAGA  TCTGGGCCCA  TGCGCCCGCG  GATCGATGCT  CACTCAAAGG  CGGTAATACG  2520
2521  GTTATCCACA  GAATCAGGGG  ATAACGCAGG  AAAGAACATG  TGAGCAAAAG  GCCAGCAAAA  2580
2581  GGCCAGGAAC  CGTAAAAAGG  CCGCGTTGCT  GGCGTTTTTC  CATAGGCTCC  GCCCCCTGA   2640
2641  CGAGCATCAC  AAAAATCGAC  GCTCAAGTCA  GAGGTGGCGA  AACCCGACAG  GACTATAAAG  2700
```

Fig. 13 cont.

```
2701 ATACCAGGCG TTTCCCCCTG GAAGCTCCCT CGTGCGCTCT CCTGTTCCGA CCCTGCCGCT 2760
2761 TACCGGATAC CTGTCCGCCT TTCTCCCTTC GGGAAGCGTG GCGCTTTCTC AATGCTCACG 2820
2821 CTGTAGGTAT CTCAGTTCGG TGTAGGTCGT TCGCTCCAAG CTGGGCTGTG TGCACGAACC 2880
2881 CCCCGTTCAG CCCGACCGCT GCGCCTTATC CGGTAACTAT CGTCTTGAGT CCAACCCGGT 2940
2941 AAGACACGAC TTATCGCCAC TGGCAGCAGC CACTGTGTAAC AGGATTAGCA GAGCGAGGTA 3000
3001 TGTAGGCGGT GCTACAGAGT TCTTGAAGTG GTGGCCTAAC TACGGCTACA CTAGAAGGAC 3060
3061 AGTATTTGGT ATCTCGCTCT TGCTGAAGCC AGTTACCTTC GGAAAAAGAG TTGGTAGCTC 3120
3121 TTGATCCGGC AACAAACCA CCGCTGGTAG CGGTGGTTTT TTTGTTTGCA AGCAGCAGAT 3180
3181 TACGCGCAGA AAAAAAGGAT CTCAAGAAGA TCCTTTGATC TTTTCTACGG GGTCTGACGC 3240
3241 TCAGTGGAAC GAAAACTCAC GTTAAGGGAT TTTGGTCATG AGATTATCAA AAAGGATCTT 3300
3301 CACCTAGATC CTTTTAAATT AAAAATGAAG TTTTAAATCA ATCTAAAGTA TATATGAGTA 3360
3361 AACTTGGTCT GACAGTTACC AATGCTTAAT CAGTGAGGCA CCTATCTCAG CGATCTGTCT 3420
3421 ATTTCGTTCA TCCATAGTTG CCTGACTCCC CGTCGTGTAG ATAACTACGA TACGGGAGGG 3480
3481 CTTACCATCT GGCCCCAGTG CTGCAATGAT ACCGCGAGAC CCACGCTCAC CGGCTCCAGA 3540
3541 TTTATCAGCA ATAAACCAGC CAGCCGGAAG GGCCGAGCGC AGAAGTGGTC CTGCAACTTT 3600
3601 ATCCGCCTCC ATCCAGTCTA TTAATTGTTG CCGGGAAGCT AGAGTAAGTA GTTCGCCAGT 3660
3661 TAATAGTTTG CGCAACGTTG TTGCCATTGC TACAGGCATC GTGGTGTCAC GCTCGTCGTT 3720
3721 TGGTATGGCT TCATTCAGCT CCGGTTCCCA ACGATCAAGG CGAGTTACAT GATCCCCCAT 3780
3781 GTTGTGCAAA AAAGCGGTTA GCTCCTTCGG TCCTCCGATC GTTGTCAGAA GTAAGTTGGC 3840
3841 CGCAGTGTTA TCACTCATGG TTATGGCAGC ACTGCATAAT TCTCTTACTG TCATGCCATC 3900
3901 CGTAAGATGC TTTTCTGTGA CTGGTGAGTA CTCAACCAAG TCATTCTGAG AATAGTGTAT 3960
3961 GCGGCGACCG AGTTGCTCTT GCCCGGCGTC AATACGGGAT AATACCGCGC CACATAGCAG 4020
4021 AACTTTAAAA GTGCTCATCA TTGGAAAACG TTCTTCGGGG CGAAAACTCT CAAGGATCTT 4080
4081 ACCGCTGTTG AGATCCAGTT CGATGTAACC CACTCGTGCA CCCAACTGAT CTTCAGCATC 4140
4141 TTTTACTTTC ACCAGCGTTT CTGGGTGAGC AAAAACAGGA AGGCAAAATG CCGCAAAAAA 4200
4201 GGGAATAAGG GCGACACGGA AATGTTGAAT ACTCATACTC TTCCTTTTTC AATATTATTG 4260
```

Fig. 13 cont.

```
                 10         20         30         40         50         60
                 |          |          |          |          |          |
4261  AAGCATTTAT CAGGGTTATT GTCTCATGAG CGGATACATA TTTGAATGTA TTTAGAAAAA  4320
4321  TAAACAAATA GGGGTTCCGC GCACATTTCC CCGAAAAGTG CCACCTGACG TCTAAGAAAC  4380
4381  CATTATTATC ATGACATTAA CCTATAAAAA TAGGCGTATC ACGAGGCCCT TTCGTCTCGC  4440
4441  GCGTTTCGGT GATGACGGTG AAAACCTCTG ACACATGCAG CTCCCGGAGA CGGTCACAGC  4500
4501  TTGTCTGTAA GCGGATGCCG GGAGCAGACA AGCCCGTCAG GGCGGTCAG  CGGGTGTTGG  4560
4561  CGGGTGTCGG GCTGGCTTA  ACTATGCGGC ATCAGAGCAG ATTGTACTGA GAGTGCAC    4618
```

METHOD FOR THE ISOLATION OF CCC PLASMID DNA

The present invention relates to the production of biomass for the isolation of ccc plasmid DNA comprising culturing a bacterial transformant in a bioreactor containing an antibiotic-free batch medium under batch-conditions and, at the end of the batch phase, feeding under feed-back conditions a portion of a feed medium after the rise of DO above a threshold-set point. Said feed medium comprises besides a carbon and a nitrogen source, a magnesium salt, preferably in concentrations above 20 mM. Preferably, the bacterial transformant is harvested after the end of the culture and frozen or freeze-dried. Also preferred is that ccc plasmid DNA is, optionally directly, isolated after harvesting the bacteria.

Several documents are cited throughout the text of this specification. Each of the documents cited herein (including any manufacturer's specifications, instructions, etc.) are hereby incorporated by reference; however, there is no admission that any document cited is indeed prior art of the present invention.

With the advent and progress of recombinant DNA technology into a variety of fields such as food stuff production and medical therapy, the desire for large quantities of highly pure DNA has constantly risen. Traditional methods of purifying genomic or plasmid DNA (see, e.g., Sambrook et al., "Molecular Cloning, A Laboratory Manual", CSH Press, $2^{nd}$ edition, 1989, Cold Spring Harbor N.Y.) usually require sophisticated methodology if the DNA is to be free from RNA and other contaminating organic compounds. In particular, methods for obtaining ccc plasmid DNA in pure form regularly suffer from the disadvantage that other plasmid topologies also produced have to be separated from the desired product. For example, Lahijani et al., Human Gene Therapy 7 (1996), 1971–1980 have reported that high yields of pBR322-derived plasmids intended for human gene therapy may be obtained when plasmids comprising a temperature-sensitive single-point mutation that affects the negative regulation of replication from the ColE1 origin of replication are employed. Using this process, a yield of 2.2 g of plasmid DNA from a 10 liter-fed batch fermentation were reported. However, the bacterial transformants were grown in the presence of the antibiotic kanamycin which would render them unsuitable for registration and subsequent use in humans. Other approaches have tried to avoid the use of antibiotics; see, e.g., Chen et al., J. Industrial Microbiology and Biotechnology 18 (1997), 43–48. In this report, an automated fed-batch fermentation with feed-back controls based on dissolved oxygen and pH for the production of supercoiled plasmid DNA is disclosed. This DNA is suggested to be useful for DNA vaccines. However, the results reported, for example in FIG. 4, do not support the suggested suitability of the plasmid DNA for vaccination purposes. This is due to the fact that besides ccc plasmid DNA a variety of other plasmid forms are produced under these conditions. Furthermore, this method leads to high contaminations with genomic DNA and, comparatively, only small plasmid amounts can be obtained.

Accordingly, ccc plasmid DNA produced by the prior art methods is unsuitable for a variety of purposes such as medical purposes due to the heterogeneity of the product obtained and/or due to the employment of antibiotics in the production process. The technical problem underlying the present invention was therefore to provide a method that overcomes these prior art difficulties and allows for the production of ccc DNA without the concomitant production of other plasmid forms and which is, moreover, suitable for medical purposes. The solution to said technical problem is achieved by providing the embodiments characterized in the claims.

Thus, the present invention relates to a method for the production of biomass for the isolation of ccc plasmid DNA comprising
   (a) culturing a bacterial transformant in a bioreactor containing an antibiotic-free batch-medium comprising
      (aa) a carbon source;
      (ab) an inorganic salt mixture;
      (ac) a nitrogen source;
      under batch-culturing conditions;
   (b) feeding under feed-back conditions to said culture of (a) at the end of the batch phase, after rising of DO above a threshold-set point, a portion of a feed-medium comprising
      (ba) a carbon source; and
      (bb) a magnesium salt; and
   (c) allowing the bacterial transformant to metabolize said feed-medium.

The term "biomass", as used in the context of the present invention, relates to any biological material that is or arises from cells or organisms that are capable of reproduction.

The term "ccc plasmid DNA" refers to a plasmid isoform that is a circular plasmid which is typically but not necessarily underwound relative to a relaxed molecule. This results in a more compact conformity of the molecule which is described as a supercoiled covalently closed circle of the plasmid DNA. In E.coli cells, two enzymes regulate the supercoiling of DNA. The gyrase introduces negative superhelical turns into the molecule while the topoisomerase I relaxes the DNA by introducing single-strand breaks. It is most preferred in accordance with the method of the invention that ccc plasmid DNA in monomeric form is produced. Indeed, the method of the invention provides this particularly desired type of plasmid usually in an amount of more than 90% of overall plasmid production. Also useful, although less preferred, is the production of dimeric ccc plasmid DNA.

The term "batch-medium" refers to the medium used in batch cultivation, i.e., in discontinuous cultivation of bacterial transformants or other microorganisms. This discontinuous cultivation is characterized by a single inoculation into fresh medium (batch medium) at the start of the cultivation until nutrients and substrates have been exhausted.

The term "feed-back conditions" relates to the supplementation of medium concentrate during fed-batch cultivation depending on cultivation parameter(s) like, e.g., DO, pH, etc., which are correlated with the growth of the microorganism.

The term "threshold-set point" in the context of the present invention is intended to mean a defined value for a parameter that is monitored during fed-batch cultivation. In case of over-reaching or under-reaching of that value a monitor signal initiates the response in the regulation of the cultivation. The person skilled in the art is in the position to determine such defined values on the basis of his common knowledge and the teachings of this invention, see, for example, example 1.

The term "DO" (concentration of dissolved oxygen) refers hereby to the amount of oxygen in a liquid in per cent of the saturation concentration.

Under the above-defined feed-batch conditions, the concentration of dissolved oxygen (DO) rises during cultivation of bacterial transformants after the consumption of nutrients such as contained in the feed-medium. Therefore, the invention relates in a preferred embodiment to a method wherein the feeding of a bacterial transformant culture comprises repeated feeding-cycles after each rising of the DO above a threshold-set point. It is well known to the person skilled in the art that feeding can be controlled and/or measured via other control parameters, like medium pH, specific growth rate of bacterial transformants, respiration coefficients or others. Nevertheless, all these parameters are interrelated and indicative of the DO. Therefore, irrespective of which parameter is actually employed as a read-out system, it allows a direct (or indirect) conclusion on the DO value. Accordingly, measurement of any of said parameters is covered by the invention as long as it allows a conclusion with respect to the rising of DO above a threshold-set point.

The term "allowing the bacterial transformant to metabolize said feed-medium" relates to the partial or complete metabolization of said feed-medium and preferably to the essentially complete metabolization of said feed medium.

In accordance with the present invention it has been found that the here disclosed method leads to the production of high plasmid concentrations and to plasmids with a DNA homogeneity of typically more than 90% ccc monomers. The result is all the more surprising since ccc monomers of the indicated high homogeneity are obtained in the absence of selection pressure by antibiotics. The person skilled in the art is able to employ the here disclosed method for the production of ccc DNA over a broad range of types or sizes of plasmids. The method of the invention in addition allows the isolation of a larger quantity of the desired plasmid from bacterial cultures than was possible with prior art methods. This also leads to a significant cost reduction of the fermentation processes since smaller fermentors may be employed as compared to prior art processes if the same amount of plasmid is to be generated.

A further significant advantage of the method of the present invention for the production of biomass for the isolation of ccc plasmid DNA relates to the fact that the media are devoid of antibiotics. The obtained ccc DNA is thus definitively antibiotic-free and may, without time consuming and costly further elaborate purification schedules, be employed in medical therapy where antibiotic contaminations are to be avoided.

It is most preferred in the method of the present invention to employ batch-or feed media devoid of yeast extract or other complex amino acid sources derived from natural sources. This is because the cultivation in such fully synthetic media does not bear the danger of source related contamination and has the advantage of a higher reproducibility. Another preferred option would be to use semi-synthetic media, comprising, for example, yeast extracts, plant extracts, peptone supplements and others. These synthetic or semi-synthetic media may be employed in one or more steps of the culturing of the transformants. This also includes the pre-culturing step addressed below. It is also envisaged by the present invention to cultivate in/feed different types of media at different cultivation steps. Different media may also be fed when repeated feeding cycles are employed as discussed herein below. It is most preferred that these media are autoclavable. Magnesium salts should be autoclaved separately.

As has been outlined above, in a preferred embodiment of the method of the invention, step (b) comprises repeated feeding cycles after each rising of the DO above a threshold-set point. This embodiment of the invention is particularly advantageous since it allows the production of high yields of biomass which allows for the isolation of high amounts of ccc-plasmid DNA.

The bacterial transformant used in the method of the invention can be either a gram-negative or a gram-positive bacterium. Examples of gram-positive bacteria are bacteria of the genus Bacillus, for example *Bacillus subtilis*. In a preferred embodiment, the bacterial transformant is an *E. coli* cell.

Whereas the person skilled in the art is capable of devising or preparing a suitable carbon source, glycerol is preferably used as a carbon source in the method of the present invention.

A variety of well known and established nitrogen sources may be employed in the method of the invention. In a further preferred embodiment of the present invention, the nitrogen source employed is $NH_3$.

In a further preferred embodiment of the method of the invention the carbon source in the batch-medium is in a (initial final) concentration of $\leq 100$ g/l.

In another preferred embodiment of the method of the invention the carbon source in the feed-medium is in a (initial final) concentration of $\leq 1000$ g/l.

In yet another preferred embodiment of the method of the invention the nitrogen source is in a (initial final) concentration of $\leq 30\%$.

In a further preferred embodiment of the method of the invention the inorganic salt mixture comprises $Na_2HPO_4 \leq 6$ g/l, $KH_2PO_4 \leq 3$ g/l, $NaCl \leq 0.5$ g/l, and citric acid.$H_2O \leq 1.5$ g/l. This refers to the initial final concentration in the medium, i.e. the final concentration that is present in the medium at the onset of fermentation.

Most preferably, said inorganic salt mixture also comprises a magnesium salt, preferably $MgSO_4$, for example complexed with water. In this case, an initial concentration of smaller than or about 0.3 g/l is preferred. It is also desired that the magnesium salt is autoclaved separately.

In another preferred embodiment of the method of the invention in step (b) the magnesium salt concentration is in a range of 5–100 mM. This again refers to the initial final concentration in the medium.

In a particularly preferred embodiment of the method of the invention in step (b) the magnesium salt concentration is 80 mM. In accordance with the invention, it has surprisingly been found that in particular rather high magnesium salt concentrations such as 80 mM, preferrebly of $MgSO_4$, yield excellent results with regard to the homogeneity of the ccc plasmid monomers.

Magnesium salts that may be used in accordance with the present invention comprises $MgCl_2$, $Mg(NO_3)_2$, $MgSO_4$ or others. In a preferred embodiment of the method of the invention the magnesium salt is $MgSO_4$.

In another preferred embodiment of the invention a solution of trace elements is added in steps (a) and/or (b). Addition of trace elements may further enhance the plasmid yield.

In another embodiment of the method of the invention the solution of trace elements comprises each of the following compounds $FeCl_3.6H_2O$ in a final concentration of preferably $\leq 54.0$ mg/l $ZnSO_4.7H_2O$ in a final concentration of preferably $\leq 13.8$ mg/l $MnSO_4.H_2O$ in a final concentration of preferably $\leq 18.5$ mg/l $CoSO_4.7H_2O$ in a final concentration of preferably $\leq 5.6$ mg/l $CuCl_2$ in a final concentration of preferably $\leq 1.7$ m/l $H_3BO_3$ in a final concentration of preferably $\leq 10$ mg/l $Na_2MoO4.2H_2O$ in a final concentration of preferably $\leq 25$ mg/l; and citric acid in a final concentration of preferably $\leq 50$ mg/l Bacterial or prokaryotic growth media can advantageously be supplemented with an amino acid source. Therefore, in a further preferred embodiment of the method of the invention, the batch-medium comprises an amino acid source.

In another preferred embodiment of the method of the invention the feed-medium comprises an amino acid source. Amino acid sources are well known to the person skilled in the art and can comprise yeast extracts, plant extracts, peptone supplements and others (see Sambrook et al., loc. cit.).

In a further embodiment of the method of the invention the culturing of the bacterial transtormant is carried out at a temperature range of 30° C. to 42° C.

In a particularly preferred embodiment of the method of the invention the temperature range is about 35° C. to 38° C.

In order to compensate auxotrophic requirements of bacterial transformants, it is preferred that in the method of the invention the batch-medium comprises a bacterial host strain specific supplement. A variety of specific supplements for different bacterial host strains has been described and is well known in the art, e.g., thiamine for bacterial transformants carrying a thiamine deficiency.

In a further preferred embodiment of the method of the invention the host cells are harvested, after step (c), from said cultures. Harvesting of bacterial transformants is one of the conventional methods in fermentation and molecular biology techniques. The harvest of transformants can comprise filtering, centrifugation or similar methods which are well known in the art.

In yet another preferred embodiment of the method of the invention, the host cells are, after step (c), subjected to a washing step before or after harvesting. These washing steps can be carried out in a solution that does not affect the integrity of the cells but removes culturing compounds from the cell.

In another preferred embodiment of the method of the invention, a further step comprises the freezing or freeze-drying of the transformants after step (c) or after the steps identified herein above in any of the further preferred embodiments. The embodiment is particularly useful if an immediate isolation of ccc plasmid is not desired. Frozen or freeze-dried cells may be conveniently be shipped or stored until further use.

In yet another preferred embodiment of the method of the invention a further step comprises the isolation of ccc DNA.

There are multiple ways to isolate ccc DNA which are well know to the person skilled in the art. These include CsCl gradient centrifugation and chromatography purification methods (see, e.g., Sambrook et al., "Molecular Cloning, A Laboratory Manual", CSH Press, $2^{nd}$ edition, 1989, Cold Spring Harbor N.Y.).

As stated herein above, isolated plasmid DNA consisting of more than 90% ccc monomers may be obtained. The person skilled in the art, when employing the teachings of the present invention, is able to obtain ccc DNA in large quantities which fulfills the quality criteria of plasmid DNA for gene therapeutic and nucleic acid vaccination approaches (see Schorr et al., DNA Vaccines 772 (1995), 271–273) without subsequent exhaustive purification steps to get rid, for example, of antibiotics. Thus, it is possible to employ the obtained ccc DNA of the invention for nucleic acid vaccinations as described in the prior art, for example in Davis et al., Vaccine 12 (1994), 1503–1509, or for gene therapeutic strategies as disclosed in Cao et al., Human Gene Therapy 6 (1995), 1497–1501.

Furthermore, in another preferred embodiment, the invention relates to a method further comprising the step of (a') pre-culturing the bacterial transformant in an antibiotic-free medium.

In a particularly preferred embodiment of the method of the invention the bacterial transformant is in exponential growth phase after the end of said pre-culturing. The exponential growth phase may be assessed by conventional technology, for example, by determining the optical density of the culture broth.

The figures show

FIG. 1: Time-course of dissolved oxygen, agitation speed and feed medium as monitored in a bioreactor during a DO feed-back controlled fed-batch cultivation. Shown is the cultivation of the plasmid pUK21CMVβ in E coli DH5α in a 30 L-bioreactor. Above a threshold set-point of 30%, DO was controlled by increasing agitation speed. Below a threshold set-point of 45%, the DO was controlled by feeding a nutrient solution into the bioreactor.

Figure 2:
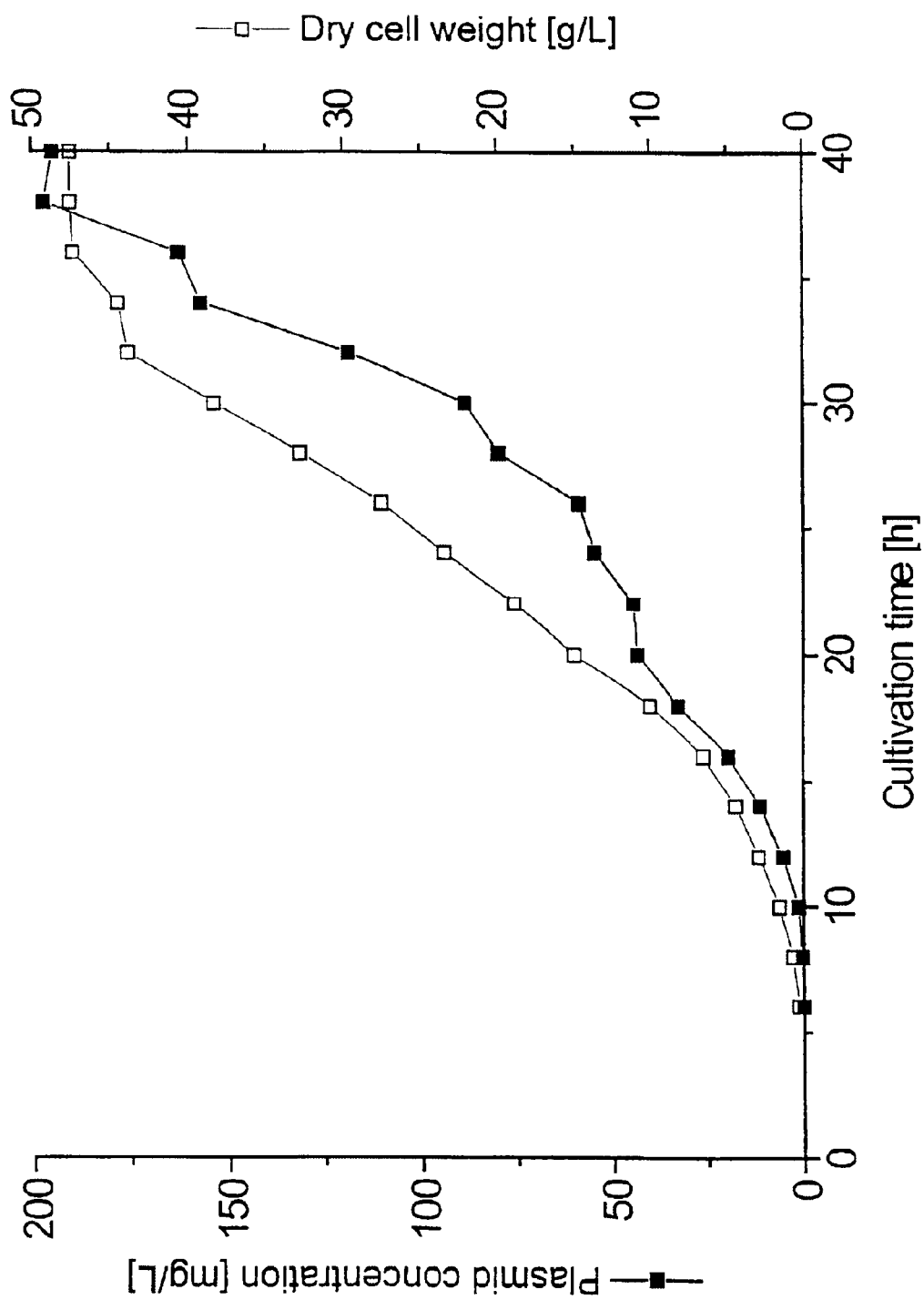

FIG. 2: Dry cell weight (DCW) and plasmid concentration during fed-batch cultivation of pUK21CMVβ in E. coli DH5α in semi-defined glycerol-yeast extract medium. The bacterial transformant was cultivated in a 30 I-bioreactor.

Figure 3:
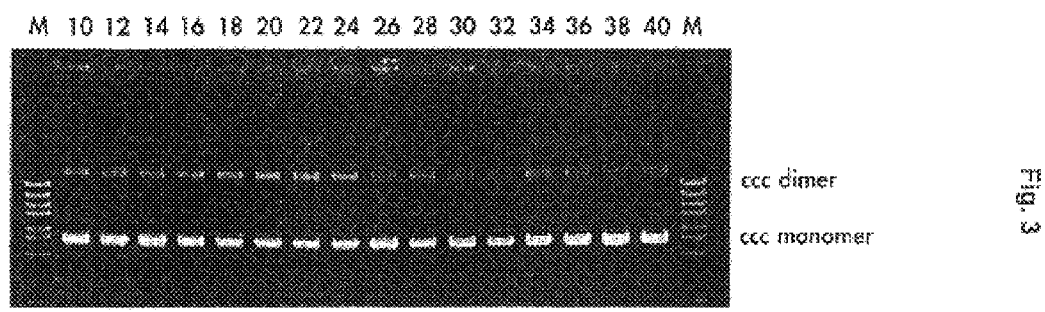

FIG. 3: 0.8% Agarose gel electrophoresis of plasmid DNA (each about 250 ng) at different cultivation times (10–40 h) of a 30 liter cultivation. Plasmid DNA was isolated from defined culture volumes using QIAGEN Miniprep kits.

Figure 4:
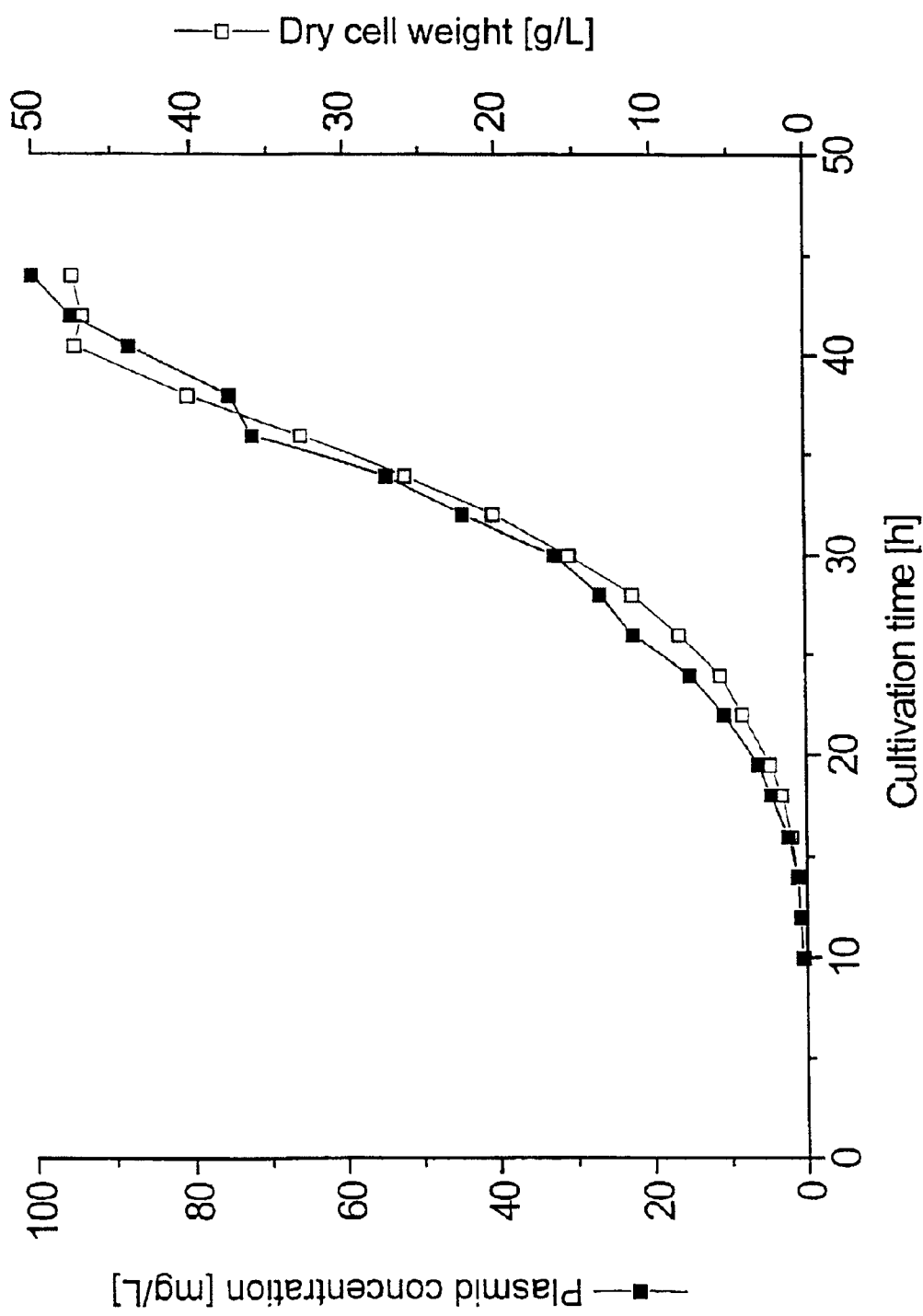

FIG. 4: Dry cell weight and plasmid concentration during fed-batch cultivation of E. Coli DH5α containing pUK21CMVβ, using a synthetic glycerol medium. Fermentation was carried out in a 5 L-bioreactor.

Figure 5:
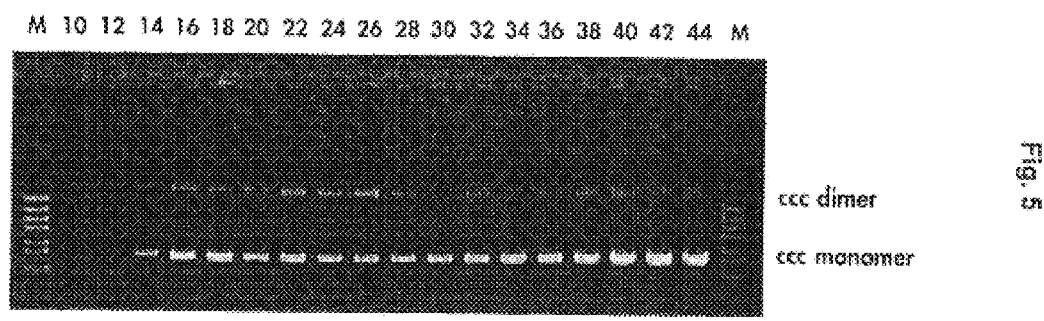

FIG. 5: 0.8% Agarose gel electrophoresis of plasmid DNA (each about 250 ng) at different cultivation times (10–44 h) of a 7 liter cultivation. Plasmid DNA was isolated from defined culture volumes using QIAGEN Miniprep kits.

Figure 6:
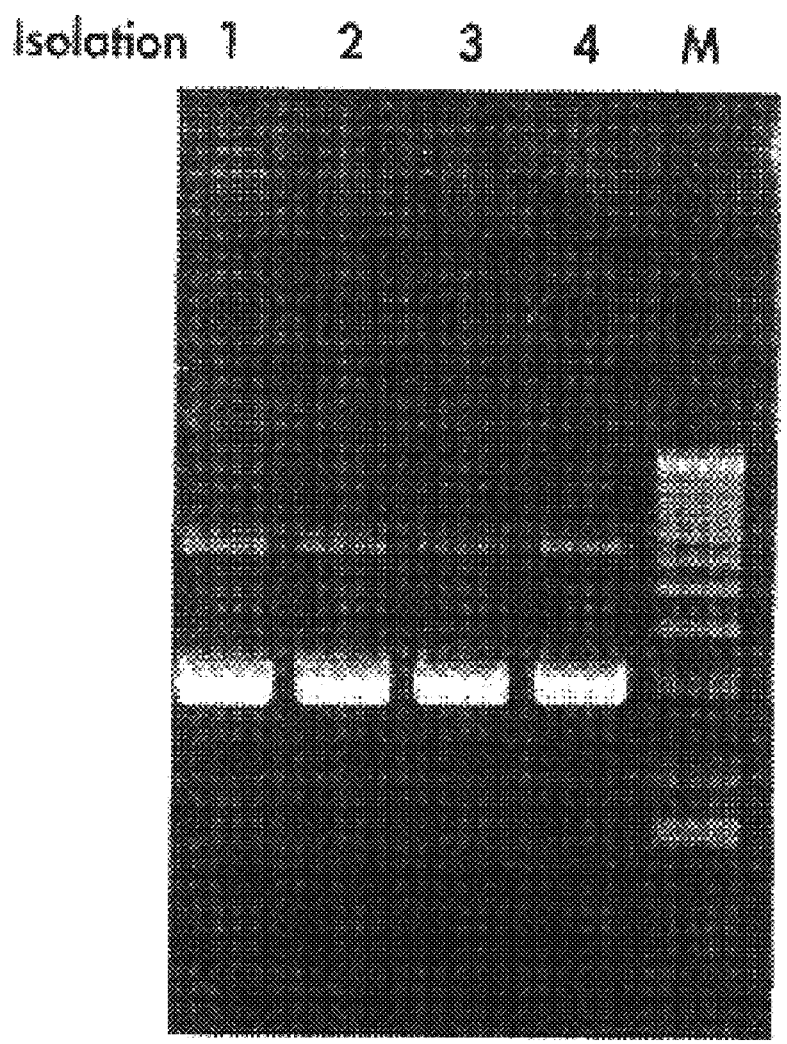

FIG. 6: 0.8% Agarose gel electrophoresis of pUT 649 plasmid DNA samples (200 ng/4 different isolates) at 41 h cultivation time, when cells were harvested. Plasmid DNA was independently isolated using QIAGEN Midiprep kits (Tip-100).

Figure 7:
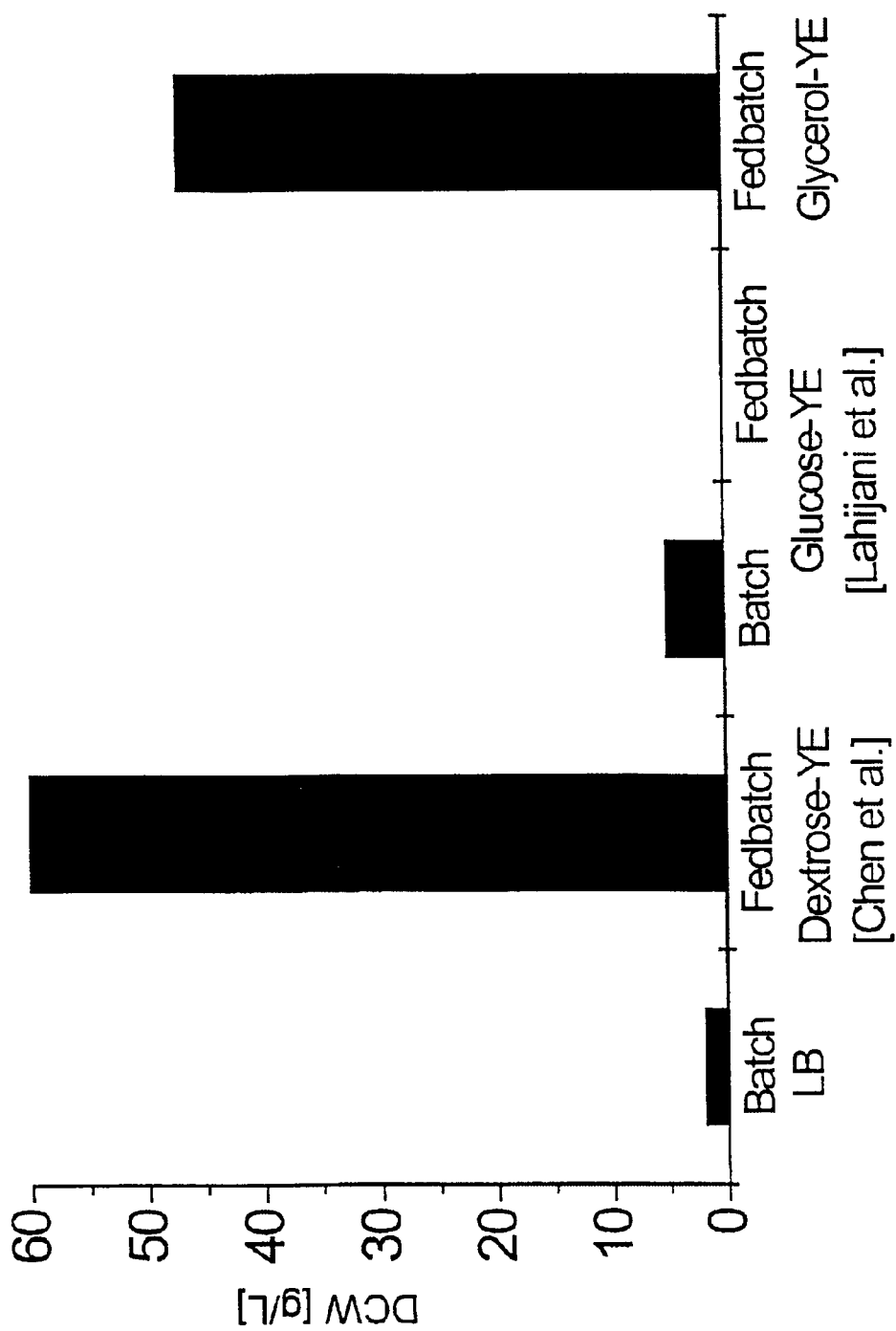

FIG. 7: Final biomass of several cultivation conditions in yeast-extract (YE) media. Cultivations were performed as described in example 1 or described by Chen et al., J. Industrial Microbiology and Biotechnology 18 (1997), 43–48 or Lahijani et al., Human Gene Therapy 7 (1996), 1971–1980.

Figure 8:
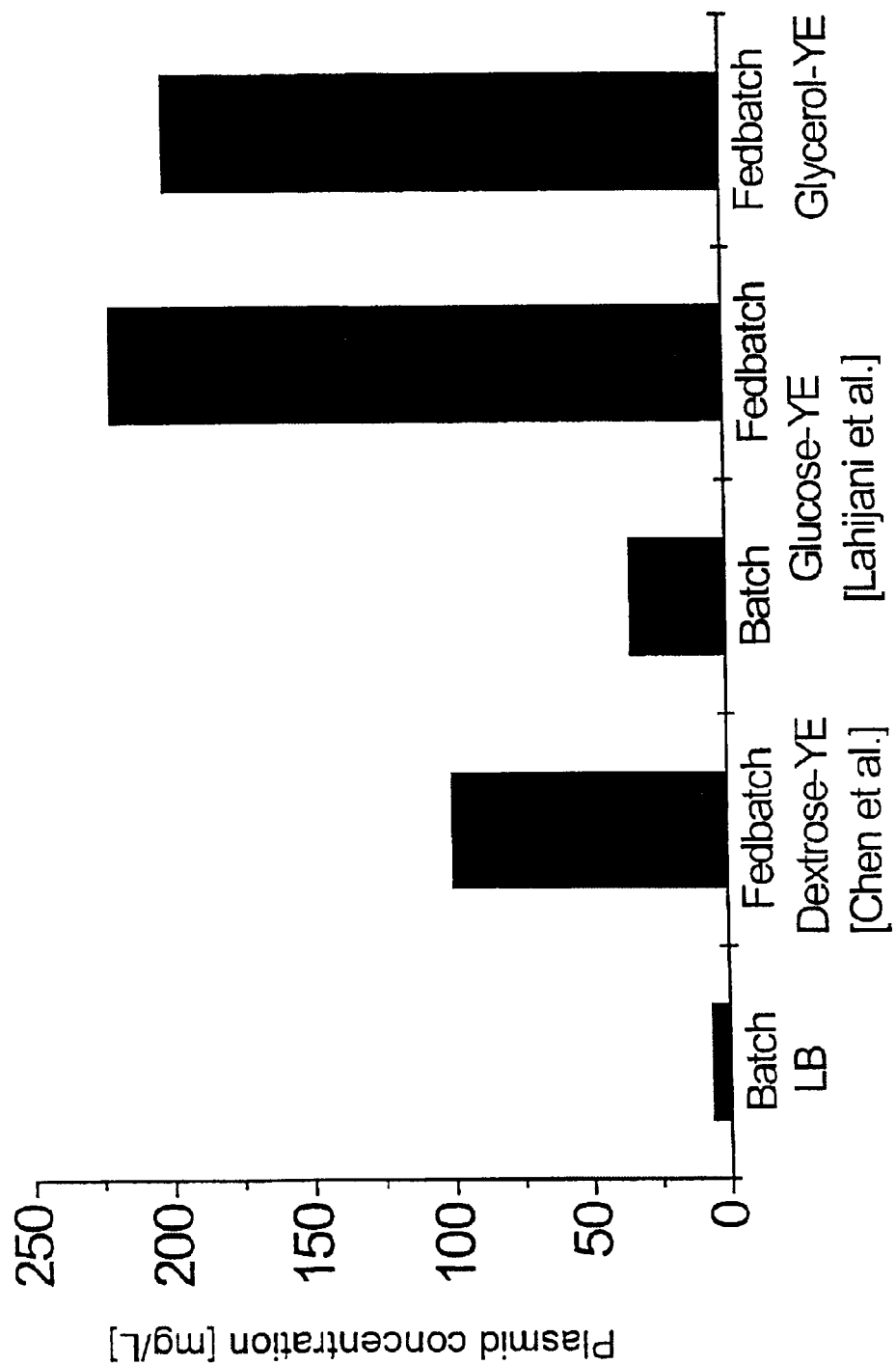

FIG. 8: Final plasmid concentration of several cultivations in yeast-extract (YE) media. Cultivation was carried out as described in example 1 and compared to cultivations as described by Chen et al., J. Industrial Microbiology and Biotechnology 18 (1997), 43–48 or Lahijani et al., Human Gene Therapy 7 (1996), 1971–1980.

Figure 9:
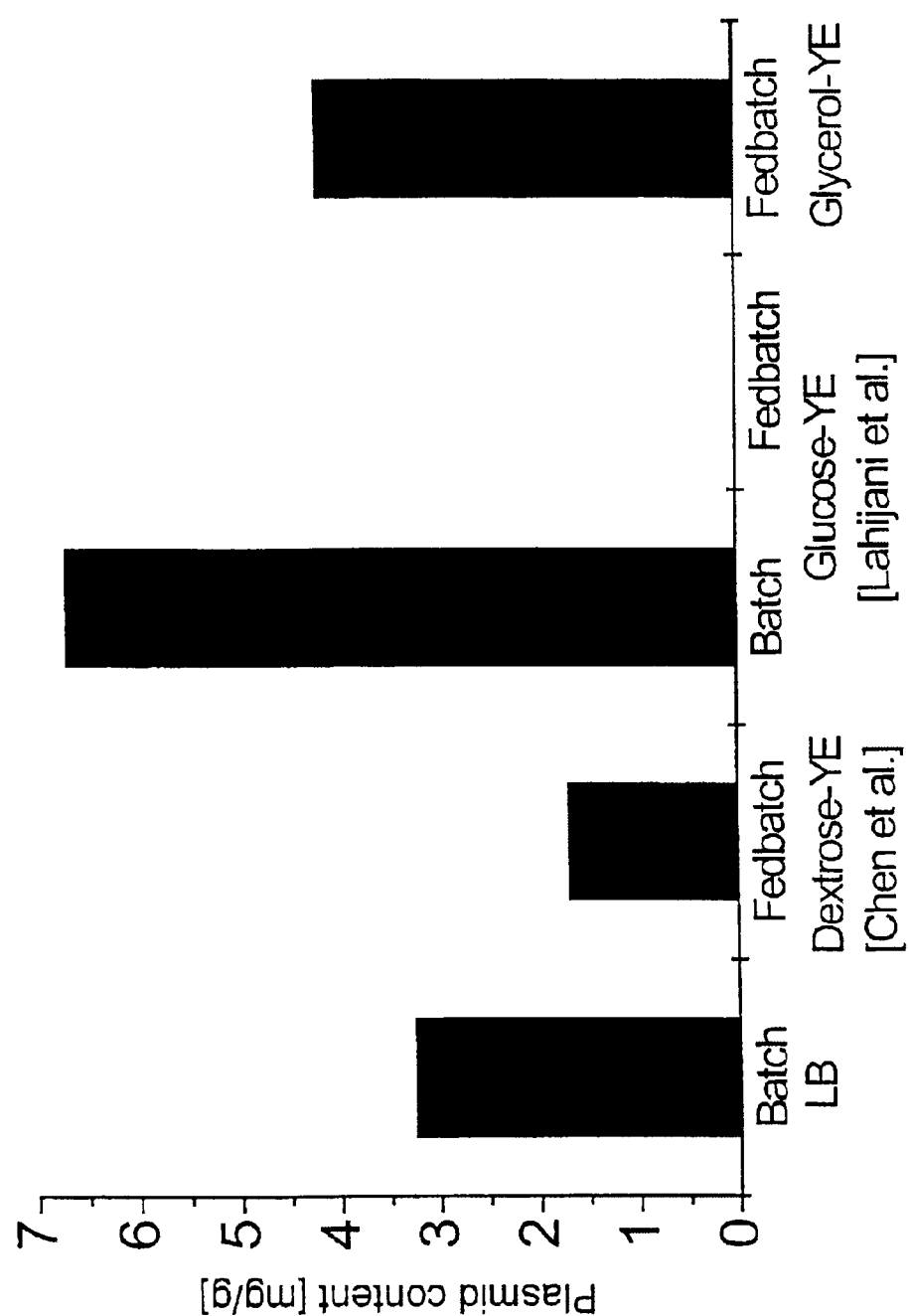

FIG. 9: Plasmid yield per biomass of several cultivations in yeast-extract (YE) media at cell harvest. Cultivation was carried out as described in example 1 and compared to cultivations as described by Chen et al., J. Industrial Microbiology and Biotechnology 18 (1997), 43–48 or Lahijani et al., Human Gene Therapy 7 (1996), 1971–1980.

Figure 10:
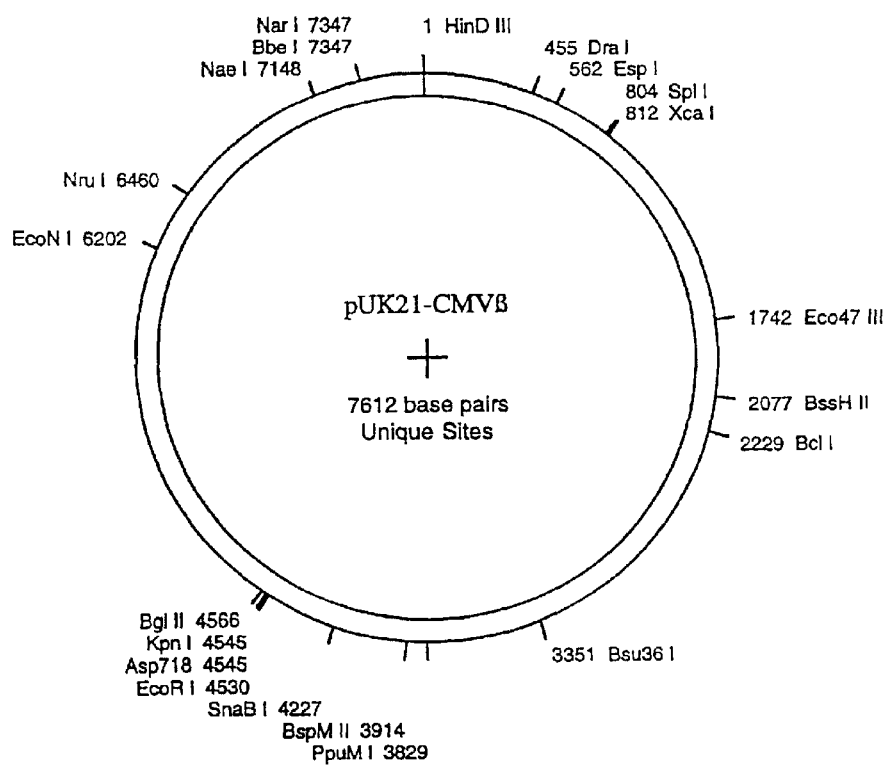

FIG. 10: Restriction map of plasmid pUK21CMVβ.

FIG. 11: DNA sequence of plasmid pUK21CMVβ (SEQ ID NO: 2).

Figure 12:
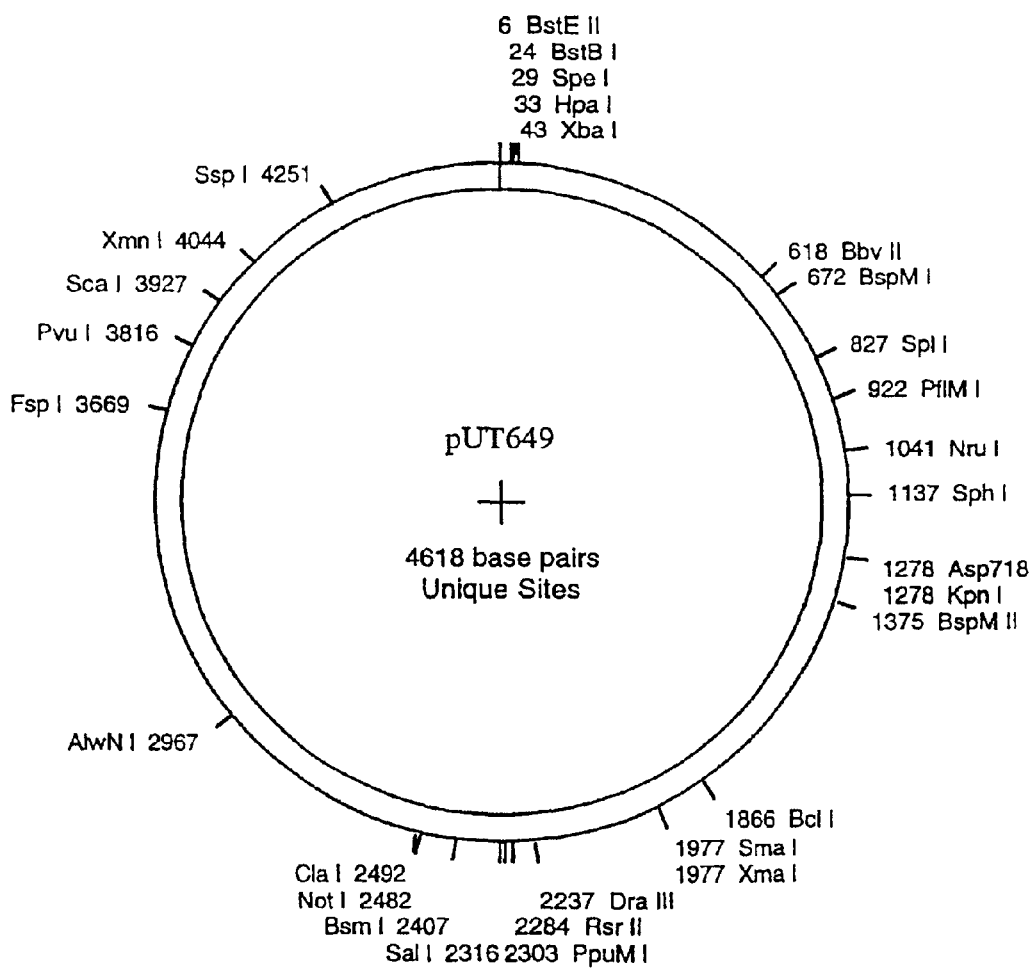

FIG. 12: Restriction map of plasmid pUT 649.
FIG. 13: DNA sequence of plasmid pUT 649 (SEQ ID NO: 1).
The examples illustrate the invention.

EXAMPLE 1

High-quality and High-quantity Production of a 7.6 kbp ccc Plasmid in Glycerol/yeast Media The method for the production of biomass for the isolation of ccc plasmid DNA has been carried out by a feed-back controlled fed-batch cultivation of *Escherichia coli* DH5α containing the plasmid pUK21CMVβ (7612 bp) (FIGS. 10, 11 SEQ ID NO; 2) in a 30-L bioreactor (LAB 30 L, MBR, Switzerland) with a working volume of 23 l. The semi-defined batch medium (15 l) consisted of 10 g/l glycerol, 5.0 g/l yeast extract, 6.0 g/l $Na_2HPO4$, 3.0 g/l $KH_2HPO_4$, 0.5 g/l NaCl, 1.5 g/l citric acid, 0.3 g/l $MgSO_4.7H_2O$, 5 mg/l thiamin hydrochloride and 10 ml/l trace element solution. Thiamin hydrochloride and the stock solution of trace elements (5.40 g/l $FeCl_3.H_2O$, 1.38 g/l $ZnSO_4.7H_2O$, 1.85 g/l $MnSO_4.H_2O$, 0.56 g/l $CoSO_4.7H_2O$, 0.17 g/l $CuCl_2$, 1.0 g/l $H_3BO_3$, 2.5 g/l $Na_2MoO_4.2H_2O$ and 5.0 g/l citric acid) were sterilized separately. Before sterilization of the bioreactor (25 min at 121° C.), the pH of the medium was adjusted to 6.7 using NaOH.

Cultivation was carried out at 37° C. and 0.5 bar. Aeration was maintained at 30 l/min and pH was controlled by 10% $H_3PO_4$ and/or 25% $NH_4OH$. As antifoam reagent Pluronic® PE-8100 (BASF) was used. Minimum agitation speed was 100 rpm.

A frozen glycerol stock of *E. coli* DH5α including pUK21CMVβ was used to inoculate 200 ml of Luria-Bertani (LB) seed medium in a 1000 ml shake flask. The culture was incubated at 37° C. for 8 h on an orbital shaker at 180 rpm. After reaching a cell idensity of $OD_{600}$ 0.3–0.5, a 50 ml aliquot of this pre-culture was transferred into the bioreactor.

During cultivation, dissolved oxygen (DO) was automatically kept at 30% air saturation by increasing the agitation speed by 1% of the previous agitation speed when dissolved oxygen concentration went below a threshold set-point of 30%. At DO concentrations above 30%, the agitation speed stayed constant. When the DO reached a threshold set-point of 45% air saturation, a nutrient pump was automatically activated to feed a concentrated solution of 600 g/l glycerol, 90 g/l yeast extract and 20 g/l $MgSO_4*7H_2O$ to the culture. The maximum flow rate of the nutrient pump was 50 ml/min. Feeding was interrupted when DO went below 45%. Every two hours cell growth was determined by measuring optical density at 600 nm and dry cell weight. Plasmid concentration was determined after isolating plasmid DNA from a defined pelleted culture volume using QIAGEN Miniprep kits (Tip-20) according to the instructions of the manufacturer. After digestion with restriction endonucleases EcoRI, quantification of these DNA samples was performed by capillary gel electrophoresis as described by Schmidt et al., J. Biotechnol 49 (1996), 219–229. In order to analyze the plasmid form distribution and as quality control, electrophoresis of all undigested samples was performed on 0.8% agarose gels.

FIG. 1 describes DO levels, agitation speed and feed solution values as monitored in the bioreactor during a DO feed-back controlled fed-batch cultivation. After 14 h, when the nutrients were depleted, DO concentration increased dramatically and the feeding loop started. During this fed-batch phase the DO concentration oscillated between the threshold set-point for feeding (45%) and the threshold set-point for increasing agitation speed (30%).

FIG. 2 illustrates the formation of biomass (dry cell weight) and plasmid DNA during the cultivation. Cell growth occurred until 36 h cultivation time. A final biomass of 48 g/l dry cell weight ($OD_{600}$=140) was reached. The plasmid concentration produced in this reactor was about 200 mg/l, which corresponds to 4,6 g plasmid DNA. The plasmid mass per cell weight was about 4,2 mg/g. Although no antibiotics for selection were used, plasmid concentration increased during the whole cultivation.

Agarose gel electrophoresis showed a high quality plasmid product during the whole cultivation (FIG. 3). The isolated plasmid DNA consisted of more than 90% ccc molecules and fulfilled the quality criteria of plasmid DNA for gene therapeutic and nucleic acid vaccination approaches (Schorr et al., DNA Vaccines 772 (1995), 271–273).

EXAMPLE 2

High-quality Production of ccc Plasmid DNA in Synthetic Glycerol Media

DO feed-back controlled fed-batch cultivation of *E. coli* DH5α containing pUK21CMVβ (7612 bp; SEQ ID NO: 2) was performed in a 7-L bioreactor (LAB 7 L, MBR, Switzerland) with 5,5 l working volume. Synthetic glycerol media were employed in this fermentation.

The defined batch medium (3,5 l) consisted of 20 g/l glycerol, 6.0 g/l $Na_2HPO4$, 3.0 g/l $KH_2HPO_4$, 0.5 g/l NaCl, 1.5 g/l citric acid, 0.3 g/l $MgSO_4.7H_2O$, and 10 ml/l trace element solution, containing 5.40 g/l $FeCl_3.6H_2O$, 1.38 g/l $ZnSO_4.7H_2O$, 1.85 g/l $MnSO_4.H_2O$, 0.56 g/l $CoSO_4.7H_2O$, 0.17 g/l $CuCl_2$, 1.0 g/l $H_3BO_3$. 2.5 g/l $Na_2MoO_4.2H_2O$ and 5.0 g/l citric acid. 5 mg/l thiamine hydrochloride was sterilized separately by filtration and was transferred into the bioreactor. Before sterilization of the bioreactor (25 min at 121° C.) the pH of the medium was adjusted to 6.7. Cultivation was carried out at 37° C. and 0.5 bar. Aeration was maintained at 10 l/min and the pH was controlled by 10% $H_3PO_4$ and/or 25% $NH_4OH$. Antifoam reagent was Pluronic® PE-8100 (BASF). Minimum agitation speed was 150 rpm. A frozen glycerol stock of *E. coli* DH5α including pUK21 CMVβ was used to inoculate 55 ml LB seed medium in a 300 ml shake flask. The culture was incubated at 37° C. for 8 h on an orbital shaker at 180 rpm. After reaching a cell density of $OD_{600}$ 0.3–0.5 50 ml of this pre-culture was transferred into the bioreactor.

During cultivation dissolved oxygen (DO) was automatically kept at 30% air saturation by increasing the agitation speed by 1% of the previous agitation speed, when dissolved oxygen concentration went below 30%. At DO concentrations above 30% air saturation, the agitation speed stayed constant. If DO was above 45% air saturation, a nutrient pump was activated automatically to feed a concentrated solution of 1000 g/l glycerol and 20 g/l $MgSO_4.7H_2O$ to the culture. The maximum flow rate of the nutrient pump was 30 ml/min. Feeding was interrupted when DO went below 45%.

Every two hours cell growth was determined by measuring optical density at 600 nm and dry cell weight. Plasmid concentration was determined after isolating plasmid DNA from a defined pelleted culture volume using QIAGEN Miniprep kits (Tip-20) according to the instructions of the manufacturer. After digestion with restriction endonuclease EcoRI, quantification of these DNA samples was performed by capillary gel electrophoresis as described by Schmidt et al. 1996 (Schmidt et al., *J. Biotechnol.* 49 (1996), 219–229). In order to analyze the plasmid form distribution and as quality control, electrophoresis of all undigested samples was performed on 0.8% agarose gels.

FIG. 4 describes the formation of biomass and plasmid DNA during the cultivation. Cell growth occurred until 40 h cultivation time. A final biomass of 48 g/l dry cell weight ($OD_{600}$=145) was reached using a synthetic medium. The produced plasmid concentration was about 100 mg/l, which corresponds to 550 mg plasmid DNA. The obtained plasmid mass per cell weight was about 2,1 mg/g.

As verified by agarose gel electrophoresis, plasmid product was obtained in a high quantity during the whole cultivation time (FIG. 5). The isolated plasmid DNA was obtained as ccc monomers. ccc dimers, which existed as concatemers, were found in small quantities. The DNA samples fulfilled the quality criteria of plasmid DNA for gene therapeutic and nucleic acid vaccination approaches.

EXAMPLE 3

High-quality Production of a Plasmid for Gene Therapeutic Approaches by High-salt Density Fermentation A DO feed-back controlled fed-batch cultivation of *E. coli* DH5α containing pUT 649 (FIGS. 12, 13) (4618 bp; SEQ ID NO: 1) (The pUT 649 vector has been described in the Eurogentec-catalogue 1994 (Eurogentec, Liège, Belgium) under catalogue number VE-1134-a) was performed using the same glycerol yeast-extract media (7.5 l batch medium) as described in example 1. Similar cultivation conditions as described in example 1 were applied and the fermentation was performed in a bioreactor with 10 l working volume (BRAUN BioE). Aeration was 15 l/min. In the batch phase, the agitation speed was set to 800 rpm. In the fed-batch phase, this speed was raised by 100 rpm when the DO decreased below the threshold set-point of 30%. Feed medium was pumped into the bioreactor (flow rate 10 ml/min), when the DO reached the threshold set-point 45%.

In a 1 l shake flask, 100 ml batch medium was inoculated with 500 μl glycerol stock of *E. coli* DH5α containing pUT649. Incubation was carried out for 5 h at 37° C. on an orbital shaker. An 1.5 ml inoculum of this pre-culture was transferred into the bioreactor.

After 41 h cultivation time, when bacterial transformants reached the stationary phase, the final biomass yielded 60 g/l dry cell weight and 230 mg/l of plasmid. Plasmid DNA of more than 90% ccc monomer plasmid DNA could be isolated (FIG. 6).

EXAMPLE 4

Comparison Between Different Batch and Fedbatch Culturing Conditions

Batch cultivation in Luria-Bertani-(LB) medium (Sambrook et al., loc.cit.) in a 7 L-bioreactor, fed-batch cultivation as described in example 1 and fed-batch cultivations as disclosed in the state of the art were compared. Whereas Chen et al. (J. Industrial Microbiology and Biotechnology 18 (1997), 43–48) used a dextrose-yeast extract medium in the batch phase and fed a glucose-yeast extract feed-medium, Lahijani et al. (Human Gene Therapy 7 (1996), 1971–1980) performed batch and fed-batch cultivations in antibiotic-containing glucose-yeast extract medium, employing a temperature-controllable point mutation in the bacterial transformant.

FIG. 7 shows the final biomass when cells reached the stationary growth phase. Biomass yield in batch cultivations in LB medium or described by Lahijani et al. were low. Feeding of nutrient solutions, as described by Chen et al. or as described in the present invention, led to higher biomass yields.

As shown in FIG. 8, in comparison to batch cultivations in LB medium, plasmid concentrations were increased by a factor 35–40 in fedbatch fermentations using glucose-yeast extract media, as described in Lahijani et al. or using glycerol-yeast extract media. as described in the present invention. However, fedbatch cultivations as carried out by Chen et al. led to lower plasmid concentrations.

Lahijani et al. used the antibiotic kanamycin during culturing and obtained a similar plasmid concentration as it was obtained with the method of the present invention, using antibiotic-free glycerol-yeast extract media. A comparison of biomass could not be carried out since Lahijani et al. did not disclose any figures concerning biomass obtained.

As depicted in FIG. 9, fedbatch cultivation in glycerol-yeast extract medium led to higher plasmid yields per biomass as compared to batch conditions in LB medium. Highest plasmid yields per biomass could be obtained by batch cultivation in glucose yeast extract medium but the total plasmid yield was low.

The homogeneity and purity of isolated plasmid DNA was best under cultivation conditions performed according to the present invention (FIGS. 3, 5, 6). Lahijani et al. reported that the isolated DNA contained large amounts of RNA and concatenated dimers, whereas Chen et al. obtained large amounts of contaminating genomic DNA. Hence, the removal of such contaminating non-ccc DNA, RNA or genomic DNA requires additional processing steps, is time consuming and further reduces the yields of DNA isolated by prior art technologies.

In summary, the analysis of data allows the unambiguous conclusion that the method of the invention is superior of the prior art with regard to purity of the desired product, optionally or preferably in combination with the amount of desired end product obtained. The method of the invention is applicable to other plasmids and yields similar or the same advantageous results.

What is claimed is:

1. A method for the production of biomass suitable for the isolation of covalently closed circular (ccc) monomer plasmid DNA in high yield comprising:
   (a) culturing a bacterial transformant in a bio-reactor containing an antibiotic-free batch-medium comprising
      (aa) a carbon source;
      (ab) an inorganic salt mixture;
      (ac) a nitrogen source;
      under batch-culturing conditions;
   (b) feeding under feed-back conditions to said culture of (a) at the end of the batch phase, after rising of the dissolved oxygen above a threshold-set point, a portion of a feed-medium comprising
      (ba) a carbon source; and
      (bb) a magnesium salt; and
   (c) allowing the bacterial transformant to metabolize said feed-medium, such that the isolable plasmid DNA from said bacterial transformant culture is greater than 90% ccc monomer plasmid DNA.

2. The method according to claim 1, wherein step (b) comprises repeated feeding cycles after each rising of the dissolved oxygen above a threshold-set point.

3. The method according to claim 1 or 2, wherein the bacterial transformant is an *Escherichia coli* cell.

4. The method according to claim 1 to 2, wherein glycerol is used as a carbon source.

5. The method according to claim 1 or 2, wherein $NH_3$ is used as a nitrogen source.

6. The method according to claim 1 or 2, wherein the carbon source in the batch-medium is in a concentration of $\leq 100$ g/l.

7. The method according to claim 1 or 2, wherein the carbon source in the feed-medium is in a concentration of $\leq 1000$ g/l.

8. The method according to claim 1 or 2, wherein the nitrogen source is in a concentration of $\leq 30\%$.

9. The method according to claim 1 or 2, wherein the inorganic salt mixture comprises $Na_2HPO_4 \leq 6$ g/l, $KH_2PO_4 \leq 3$ g/l, $NaCl \leq 0.5$ g/l and citric acid.$H_2O \leq 1.5$ g/l.

10. The method according to claim 9, wherein said inorganic salt mixture also comprises a magnesium salt.

11. The method according to claim 10, wherein said magnesium salt is $MgSO_4$, in a concentration of 0.3 g/l.

12. The method according to claim 1 or 2, wherein in step (b), the magnesium salt concentration is in a range of 5 to 100 mM.

13. The method according to claim 12 wherein in step (b) magnesium salt concentration is 80 mM.

14. The method according to claim 13, wherein the magnesium salt is $MgSO_4$.

15. The method according to claim 1 or 2, wherein a solution of trace elements is added in step (a) and/or (b).

16. The method according to claim 15, wherein the solution of trace elements comprises: $FeCl_3.6H_2O$, $ZnSO_4.7H_2O$, $MnSO_4.H_2O$, $CoSO_4.7H_2O$, $CuCl_2$, $H_3BO_3$, $Na_2MoO4.2H_2O$ and citric acid.

17. The method according to claim 1 or 2, wherein the batch-medium comprises an amino acid source.

18. The method according to claim 1 or 2, wherein the feed-medium comprises an amino acid source.

19. The method according claim 1 or 2, wherein the culturing of the bacterial transformant is carried out at a temperature range of 30° C. to 42° C.

20. The method according to claim 19, wherein the temperature range is about 35° C. to 38° C.

21. The method according to claim 1 or 2, wherein the batch-medium comprises a bacterial host strain specific supplement.

22. The method according to claim 1 or 2, wherein the bacterial transformant, after step (c), is harvested from said culture.

23. The method according to claim 22, wherein the bacterial transformant, after step (c), is subjected to a washing step before or after harvesting.

24. The method according to claim 23, further comprising the step (d) of isolating ccc plasmid DNA from said bacterial transformant culture.

25. The method according to claim 1 or 2, wherein a further step, after step (c), comprises the freezing or freeze-drying of the bacterial transformant.

26. The method according to claim 25, further comprising the step (d) of isolating ccc plasmid DNA from said bacterial transformant culture.

27. The method according to claim 1 or 2, wherein a further step, after step (c), comprises the isolation of ccc plasmid DNA.

28. The method according to of claim 1 or 2, further comprising the step of (a') pre-culturing the bacterial transformant in an antibiotic-free medium.

29. The method according to claim 28, wherein the bacterial transformant is in exponential growth phase after the end of said pre-culturing.

30. The method according to claim 28, wherein the medium used for step (a') is a synthetic or a semisynthetic medium.

31. The method according to claim 1 or 2, wherein the batch-medium, the feed-medium and/or the medium used for pre-culturing is a synthetic or a semisynthetic medium.

* * * * *

SEQUENCE LISTING

<160> NUMBER OF SEQ ID NOS: 2

<210> SEQ ID NO 1
<211> LENGTH: 4618
<212> TYPE: DNA

<213> ORGANISM: Escherichia coli

<400> SEQUENCE: 1

| | | | | | |
|---|---|---|---|---|---|
| catatggtga | ccggatccac | gcgttcgaac | tagttaacta | gatctagagt | ccgttacata | 60 |
| acttacggta | aatggcccgc | ctggctgacc | gcccaacgac | ccccgcccat | tgacgtcaat | 120 |
| aatgacgtat | gttcccatag | taacgccaat | agggactttc | cattgacgtc | aatgggtgga | 180 |
| gtatttacgg | taaactgccc | acttggcagt | acatcaagtg | tatcatatgc | caagtacgcc | 240 |
| ccctattgac | gtcaatgacg | gtaaatggcc | cgcctggcat | tatgcccagt | acatgacctt | 300 |
| atgggacttt | cctacttggc | agtacatcta | cgtattagtc | atcgctatta | ccatggtgat | 360 |
| gcggttttgg | cagtacatca | atgggcgtgg | atagcggttt | gactcacggg | gatttccaag | 420 |
| tctccacccc | attgacgtca | atgggagttt | gttttggcac | caaaatcaac | gggactttcc | 480 |
| aaaatgtcgt | aacaactccg | ccccattgac | gcaaatgggc | ggtaggcgtg | tacggtggga | 540 |
| ggtctatata | agcagagctc | gtttagtgaa | ccgtcagatc | gcctggagac | gccatccacg | 600 |
| ctgttttgac | ctccatagaa | gacaccggga | ccgatccagc | ctccgcggcc | gggaacggtg | 660 |
| cattggaacg | gacctgcagc | acgtgttgac | aattaatcat | cggcatagta | tatcggcata | 720 |
| gtataatacg | actcactata | ggagggccac | catggcctcg | tacccggcc | atcaacacgc | 780 |
| gtctgcgttc | gaccaggctg | cgcgttctcg | cggccatagc | aaccgacgta | cggcgttgcg | 840 |
| ccctcgccgg | cagcaagaag | ccacggaagt | ccgcccggag | cagaaaatgc | ccacgctact | 900 |
| gcgggtttat | atagacggtc | cccacgggat | ggggaaaacc | accaccacgc | aactgctggt | 960 |
| ggccctgggt | tcgcgcgacg | atatcgtcta | cgtacccgag | ccgatgactt | actggcgggt | 1020 |
| gctgggggct | tccgagacaa | tcgcgaacat | ctacaccaca | caacaccgcc | tcgaccaggg | 1080 |
| tgagatatcg | gccggggacg | cggcggtggt | aatgacaagc | gcccagataa | caatgggcat | 1140 |
| gccttatgcc | gtgaccgacg | ccgttctggc | tcctcatatc | gggggggagg | ctgggagctc | 1200 |
| acatgccccg | cccccggccc | tcaccctcat | cttcgaccgc | catccatcg | ccgccctcct | 1260 |
| gtgctacccg | gccgcgcggt | acctatggg | cagcatgacc | cccagccgg | tgctggcgtt | 1320 |
| cgtggccctc | atcccgccga | ccttgcccgg | caccaacatc | gtgcttgggg | cccttccgga | 1380 |
| ggacagacac | atcgaccgcc | tggccaaacg | ccagcgcccc | ggcgagcggc | tggacctggc | 1440 |
| tatgctggct | gcgattcgcc | gcgtttacgg | gctacttgcc | aatacggtgc | ggtatctgca | 1500 |
| gtgcggcggg | tcgtggcggg | aggactgggg | acagctttcg | gggacggccg | tgccgcccca | 1560 |
| gggtgccgag | ccccagagca | acgcgggccc | acgaccccat | atcggggaca | cgttatttac | 1620 |
| cctgtttcgg | gcccccgagt | tgctggcccc | caacggcgac | ctgtataacg | tgtttgcctg | 1680 |
| ggccttggac | gtcttggcca | aacgcctccg | ttccatgcac | gtctttatcc | tggattacga | 1740 |
| ccaatcgccc | gccggctgcc | gggacgccct | gctgcaactt | acctccggga | tggtccagac | 1800 |
| ccacgtcacc | acccccggct | ccataccgac | gatatgcgac | ctggcgcgca | cgtttgcccg | 1860 |
| tgagatgatc | agcggagcta | atggcgtcat | ggccaagttg | accagtgccg | ttccggtgct | 1920 |
| caccgcgcgc | gacgtcgccg | gagcggtcga | gttctggacc | gaccggctcg | ggttctcccg | 1980 |
| ggacttcgtg | gaggacgact | cgccggtgt | ggtccgggac | gacgtgaccc | tgttcatcag | 2040 |
| cgcggtccag | gaccaggtgg | tgccggacaa | caccctggcc | tgggtgtggg | tgcgcggcct | 2100 |
| ggacgagctg | tacgccgagt | ggtcggaggt | cgtgtccacg | aacttccggg | acgcctccgg | 2160 |
| gccgccatg | accgagatcg | gcgagcagcc | gtggggcgg | gagttcgccc | tgcgcgaccc | 2220 |
| ggccggcaac | tgcgtgcact | tcgtggccga | ggagcaggac | tgaccgacgc | cgaccaacac | 2280 |

-continued

```
cgccggtccg acggcggccc acgggtccca gggggggtcga cctcgaaact tgtttattgc    2340
agcttataat ggttacaaat aaagcaatag catcacaaat ttcacaaata aagcattttt    2400
ttcactgcat tctagttgtg gtttgtccaa actcatcaat gtatcttatc atgtctggat    2460
ccctcggaga tctgggccca tgcggccgcg gatcgatgct cactcaaagg cggtaatacg    2520
gttatccaca gaatcagggg ataacgcagg aaagaacatg tgagcaaaag gccagcaaaa    2580
ggccaggaac cgtaaaaagg ccgcgttgct ggcgtttttc cataggctcc gcccccctga    2640
cgagcatcac aaaaatcgac gctcaagtca gaggtggcga aacccgacag gactataaag    2700
ataccaggcg tttccccctg gaagctccct cgtgcgctct cctgttccga ccctgccgct    2760
taccggatac ctgtccgcct ttctcccttc gggaagcgtg cgctttctc aatgctcacg    2820 ctgtaggtat ctcagttcgg tgtaggtcgt tcgctccaag ctgggctgtg tgcacgaacc    2880
ccccgttcag cccgaccgct cgccttatc cggtaactat cgtcttgagt ccaacccggt    2940
aagacacgac ttatcgccac tggcagcagc cactggtaac aggattagca gagcgaggta    3000
tgtaggcggt gctacagagt tcttgaagtg gtggcctaac tacggctaca ctagaaggac    3060
agtatttggt atctgcgctc tgctgaagcc agttaccttc ggaaaaagag ttggtagctc    3120
ttgatccggc aaacaaacca ccgctggtag cggtggtttt tttgtttgca agcagcagat    3180
tacgcgcaga aaaaaggat ctcaagaaga tcctttgatc ttttctacgg ggtctgacgc    3240
tcagtggaac gaaaactcac gttaagggat tttggtcatg agattatcaa aaaggatctt    3300
cacctagatc cttttaaatt aaaaatgaag ttttaaatca atctaaagta tatatgagta    3360
aacttggtct gacagttacc aatgcttaat cagtgaggca cctatctcag cgatctgtct    3420
atttcgttca tccatagttg cctgactccc cgtcgtgtag ataactacga tacggagggg    3480
cttaccatct ggccccagtg ctgcaatgat accgcgagac ccacgctcac cggctccaga    3540
tttatcagca ataaaccagc cagccggaag ggccgagcgc agaagtggtc ctgcaacttt    3600
atccgcctcc atccagtcta ttaattgttg ccgggaagct agagtaagta gttcgccagt    3660
taatagtttg cgcaacgttg ttgccattgc tacaggcatc gtggtgtcac gctcgtcgtt    3720
tggtatggct tcattcagct ccggttccca acgatcaagg cgagttacat gatccccat    3780 gttgtgcaaa aaagcggtta gctccttcgg tcctccgatc gttgtcagaa gtaagttggc    3840
cgcagtgtta tcactcatgg ttatggcagc actgcataat tctcttactg tcatgccatc    3900
cgtaagatgc ttttctgtga ctggtgagta ctcaaccaag tcattctgag aatagtgtat    3960
gcggcgaccg agttgctctt gcccggcgtc aatacgggat aataccgcgc cacatagcag    4020
aactttaaaa gtgctcatca ttggaaaacg ttcttcgggg cgaaaactct caaggatctt    4080
accgctgttg agatccagtt cgatgtaacc cactcgtgca cccaactgat cttcagcatc    4140
ttttactttc accagcgttt ctgggtgagc aaaaacagga aggcaaaatg ccgcaaaaaa    4200
gggaataagg gcgacacgga atgttgaat actcatactc ttcctttttc aatattattg    4260
aagcatttat cagggttatt gtctcatgag cggatacata tttgaatgta tttagaaaaa    4320
taaacaaata ggggttccgc gcacatttcc ccgaaaagtg ccacctgacg tctaagaaac    4380
cattattatc atgacattaa cctataaaaa taggcgtatc acgaggccct ttcgtctcgc    4440
gcgtttcggt gatgacggtg aaaacctctg acacatgcag ctcccggaga cggtcacagc    4500
ttgtctgtaa gcggatgccg ggagcagaca agcccgtcag ggcgcgtcag cgggtgttgg    4560
cgggtgtcgg ggctggctta actatgcggc atcagagcag attgtactga gagtgcac     4618
```

<210> SEQ ID NO 2
<211> LENGTH: 7612
<212> TYPE: DNA
<213> ORGANISM: Escherichia coli

<400> SEQUENCE: 2

| | | | | | |
|---|---|---|---|---|---|
| aagcttgcat | gcctgcaggt | cgactctaga | ggatccgaaa | aaacctccca | cacctccccc | 60 |
| tgaacctgaa | acataaaatg | aatgcaattg | ttgttgttaa | cttgtttatt | gcagcttata | 120 |
| atggttacaa | ataaagcaat | agcatcacaa | atttcacaaa | taaagcattt | ttttcactgc | 180 |
| attctagttg | tggtttgtcc | aaactcatca | atgtatctta | tcatgtctgg | atccccgcgg | 240 |
| ccgcctagag | tcgaggccga | gtttgtcaga | agcagacca | aacagcggtt | ggaataatag | 300 |
| cgagaacaga | gaaatagcgg | caaaaataat | acccgtatca | cttttgctga | tatggttgat | 360 |
| gtcatgtagc | caaatcggga | aaacgggaa | gtaggctccc | atgataaaaa | agtaaaagaa | 420 |
| aaagaataaa | ccgaacatcc | aaaagtttgt | gttttttaaa | tagtacataa | tggatttcct | 480 |
| tacgcgaaat | acgggcagac | atggcctgcc | cggttattat | tattttttgac | accagaccaa | 540 |
| ctggtaatgg | tagcgaccgg | cgctcagctg | taattccgcc | gatactgacg | ggctccagga | 600 |
| gtcgtcgcca | ccaatcccca | tatggaaacc | gtcgatattc | agccatgtgc | cttcttccgc | 660 |
| gtgcagcaga | tggcgatggc | tggtttccat | cagttgctgt | tgactgtagc | ggctgatgtt | 720 |
| gaactggaag | tcgccgcgcc | actggtgtgg | gccataattc | aattcgcgcg | tcccgcagcg | 780 |
| cagaccgttt | tcgctcggga | agacgtacgg | ggtatacatg | tctgacaatg | gcagatccca | 840 |
| gcggtcaaaa | caggcggcag | taaggcggtc | gggatagttt | tcttgcggcc | ctaatccgag | 900 |
| ccagtttacc | cgctctgcta | cctgcgccag | ctggcagttc | aggccaatcc | cgccggatg | 960 |
| cggtgtatcg | ctcgccactt | caacatcaac | ggtaatcgcc | atttgaccac | taccatcaat | 1020 |
| ccggtaggtt | ttccggctga | taaataaggt | tttcccctga | tgctgccacg | cgtgagcggt | 1080 |
| cgtaatcagc | accgcatcag | caagtgtatc | tgccgtgcac | tgcaacaacg | ctgcttcggc | 1140 |
| ctggtaatgc | ccgccgcct | tccagcgttc | gacccaggcg | ttagggtcaa | tgcgggtcgc | 1200 |
| ttcacttacg | ccaatgtcgt | tatccagcgg | tgcacgggtg | aactgatcgc | gcagcggcgt | 1260 |
| cagcagttgt | tttttatcgc | caatccacat | ctgtgaaaga | aagcctgact | ggcggttaaa | 1320 |
| ttgccaacgc | ttattaccca | gctcgatgca | aaaatccatt | tcgctggtgg | tcagatgcgg | 1380 |
| gatggcgtgg | gacgcggcgg | ggagcgtcac | actgaggttt | tccgccagac | gccactgctg | 1440 |
| ccaggcgctg | atgtgcccgg | cttctgacca | tgcggtcgcg | ttcggttgca | ctacgcgtac | 1500 |
| tgtgagccag | agttgcccgg | cgctctccgg | ctgcggtagt | tcaggcagtt | caatcaactg | 1560 |
| tttaccttgt | ggagcgacat | ccagaggcac | ttcaccgctt | gccagcggct | taccatccag | 1620 |
| cgccaccatc | cagtgcagga | gctcgttatc | gctatgacgg | aacaggtatt | cgctggtcac | 1680 |
| ttcgatggtt | tgcccggata | acggaactg | gaaaaactgc | tgctggtgtt | ttgcttccgt | 1740 |
| cagcgctgga | tcggcgtgc | ggtcggcaaa | gaccagaccg | ttcatacaga | actggcgatc | 1800 |
| gttcggcgta | tcgccaaaat | caccgccgta | agccgaccac | gggttgccgt | tttcatcata | 1860 |
| tttaatcagc | gactgatcca | cccagtccca | gacgaagccg | ccctgtaaac | ggggatactg | 1920 |
| acgaaacgcc | tgccagtatt | tagcgaaacc | gccaagactg | ttacccatcg | cgtgggcgta | 1980 |
| ttcgcaaagg | atcagcgggc | gcgtctctcc | aggtagcgaa | agccatttt | tgatggacca | 2040 |
| tttcggcaca | gccgggaagg | gctggtcttc | atccacgcgc | gcgtacatcg | gcaaataat | 2100 |
| atcggtggcc | gtggtgtcgg | ctccgccgcc | ttcatactgc | accgggcggg | aaggatcgac | 2160 |

```
agatttgatc cagcgataca gcgcgtcgtg attagcgccg tggcctgatt cattccccag    2220
cgaccagatg atcacactcg ggtgattacg atcgcgctgc accattcgcg ttacgcgttc    2280
gctcatcgcc ggtagccagc gcggatcatc ggtcagacga ttcattggca ccatgccgtg    2340
ggtttcaata ttggcttcat ccaccacata caggccgtag cggtcgcaca gcgtgtacca    2400
cagcggatgg ttcggataat gcgaacagcg cacggcgtta aagttgttct gcttcatcag    2460
caggatatcc tgcaccatcg tctgctcatc catgacctga ccatgcagag gatgatgctc    2520
gtgacggtta acgcctcgaa tcagcaacgg cttgccgttc agcagcagca gaccattttc    2580
aatccgcacc tcgcggaaac cgacatcgca ggcttctgct tcaatcagcg tgccgtcggc    2640
ggtgtgcagt tcaaccaccg cacgatagag attcgggatt tcggcgctcc acagtttcgg    2700
gttttcgacg ttcagacgta gtgtgacgcg atcggcataa ccaccacgct catcgataat    2760
ttcaccgccg aaaggcgcgg tgccgctggc gacctgcgtt tcaccctgcc ataaagaaac    2820
tgttacccgt aggtagtcac gcaactcgcc gcacatctga acttcagcct ccagtacagc    2880
gcggctgaaa tcatcattaa agcgagtggc aacatgaaaa tcgctgattt gtgtagtcgg    2940
tttatgcagc aacgagacgt cacggaaaat gccgctcatc cgccacatat cctgatcttc    3000
cagataactg ccgtcactcc aacgcagcac catcaccgcg aggcggtttt ctccggcgcg    3060
taaaaatgcg ctcaggtcaa attcagacgg caaacgactg tcctggccgt aaccgaccca    3120
gcgcccgttg caccacagat gaaacgccga gttaacgcca tcaaaaataa ttcgcgtctg    3180
gccttcctgt agccagcttt catcaacatt aaatgtgagc gagtaacaac ccgtcggatt    3240
ctccgtggga acaaacggcg gattgaccgt aatgggatag gttacgttgg tgtagatggg    3300
cgcatcgtaa ccgtgcatct gccagtttga ggggacgacg acagtatcgg cctcaggaag    3360
atcgcactcc agccagcttt ccggcaccgc ttctggtgcc ggaaaccagg caaagcgcca    3420
ttcgccattc aggctgcgca actgttggga agggcgatcg gtgcgggcct cttcgctatt    3480
acgccagctg gcgaaagggg gatgtgctgc aaggcgatta agttgggtaa cgccagggtt    3540
ttcccagtca cgacgttgta aaacgacggg atcgcgcttg agcagctcct tgctggtgtc    3600
cagaccaatg cctcccagac cggcaacgaa atcacgttcc ttgttggtca agtaaacga     3660 catggtgact tctttttttgc tttagcaggc tctttcgatc cccgggaatt gcggccgcgg    3720
gtacaattcc gcagctttta gagcagaagt aacacttccg tacaggccta gaagtaaagg    3780
caacatccac tgaggagcag ttctttgatt tgcaccacca ccggatccgg gacctgaaat    3840
aaaagacaaa aagactaaac ttaccagtta actttctggt ttttcagttc ctcgagtacc    3900
ggatcctcta gagtccggag gctggatcgg tcccggtgtc ttctatggag gtcaaaacag    3960
cgtggatggc gtctccaggc gatctgacgg ttcactaaac gagctctgct tatatagacc    4020
tcccaccgta cacgcctacc gcccatttgc gtcaatgggg cggagttgtt acgacatttt    4080
ggaaagtccc gttgattttg gtgccaaaac aaactcccat tgacgtcaat ggggtggaga    4140
cttgaaaatc cccgtgagtc aaaccgctat ccacgcccat tgatgtactg ccaaaaccgc    4200
atcaccatgg taatagcgat gactaatacg tagatgtact gccaagtagg aaagtcccat    4260
aaggtcatgt actgggcata atgccaggcg ggccatttac cgtcattgac gtcaataggg    4320
ggcgtacttg gcatatgata cacttgatgt actgccaagt gggcagttta ccgtaaatac    4380
tccacccatt gacgtcaatg gaaagtccct attggcgtta ctatgggaac atacgtcatt    4440
attgacgtca atgggcgggg gtcgttgggc ggtcagccag gcgggccatt taccgtaagt    4500
```

```
tatgtaacga cctgcaggca tgcaagctcg aattcgagct cccgggtacc atggcatgca    4560
tcgatagatc tcgaggcctc ggactagtgg cgtaatcatg gtcatagctg tttcctgtgt    4620
gaaattgtta tccgctcaca attccacaca acatacgagc cgcggaagca taaagtgtaa    4680 agcctgggt gcctaatgag tgagctaact cacattaatt gcgttgcgct cactgcccgc    4740
tttccagtcg ggaaacctgt cgtgccagct gcattaatga atcggccaac gcgcggggag    4800
aggcggtttg cgtattggc gctcttccgc ttcctcgctc actgactcgc tgcgctcggt    4860
cgttcggctg cggcgagcgg tatcagctca ctcaaaggcg gtaatacggt tatccacaga    4920
atcaggggat aacgcaggaa agaacatgtg agcaaaaggc cagcaaaagg ccaggaaccg    4980
taaaaaggcc gcgttgctgg cgttttttcca taggctccgc ccccctgacg agcatcacaa    5040
aaatcgacgc tcaagtcaga ggtggcgaaa cccgacagga ctataaagat accaggcgtt    5100
tccccctgga agctccctcg tgcgctctcc tgttccgacc ctgccgctta ccggatacct    5160
gtccgccttt ctcccttcgg gaagcgtggc gctttctcat agctcacgct gtaggtatct    5220
cagttcggtg taggtcgttc gctccaagct gggctgtgtg cacgaacccc ccgttcagcc    5280
cgaccgctgc gccttatccg gtaactatcg tcttgagtcc aacccggtaa gacacgactt    5340
atcgccactg gcagcagcca ctggtaacag gattagcaga gcgaggtatg taggcggtgc    5400
tacagagttc ttgaagtggt ggcctaacta cggctacact agaagaacag tatttggtat    5460
ctgcgctctg ctgaagccag ttaccttcgg aaaaagagtt ggtagctctt gatccggcaa    5520
acaaaccacc gctggtagcg gtggtttttt tgtttgcaag cagcagatta cgcgcagaaa    5580
aaaaggatct caagaagatc ctttgatctt ttctacgggg tctgacgctc agtggaacga    5640
aaactcacgt taagggattt tggtcatgag cttgcgccgt cccgtcaagt cagcgtaatg    5700
ctctgccagt gttacaacca attaaccaat tctgattaga aaaactcatc gagcatcaaa    5760
tgaaactgca atttattcat atcaggatta tcaataccat atttttgaaa agccgtttc    5820 tgtaatgaag gagaaaactc accgaggcag ttccatagga tggcaagatc ctggtatcgg    5880
tctgcgattc cgactcgtcc aacatcaata caacctatta atttccctc gtcaaaaata    5940 aggttatcaa gtgagaaatc accatgagtg acgactgaat ccggtgagaa tggcaaaagt    6000
ttatgcattt ctttccagac ttgttcaaca ggccagccat tacgctcgtc atcaaaatca    6060
ctcgcatcaa ccaaaccgtt attcattcgt gattgcgcct gagcgagacg aaatacgcga    6120
tcgctgttaa aaggacaatt acaaacagga atcgaatgca accggcgcag gaacactgcc    6180
agcgcatcaa caatattttc acctgaatca ggatattctt ctaatacctg gaatgctgtt    6240
tttccgggga tcgcagtggt gagtaaccat gcatcatcag gagtacggat aaaatgcttg    6300
atggtcggaa gaggcataaa ttccgtcagc cagtttagtc tgaccatctc atctgtaaca    6360
tcattggcaa cgctaccttt gccatgtttc agaaacaact ctggcgcatc gggcttccca    6420
tacaagcgat agattgtcgc acctgattgc ccgacattat cgcgagccca tttatacca    6480 tataaatcag catccatgtt ggaatttaat cgcggcctcg acgtttcccg ttgaatatgg    6540
ctcataacac cccttgtatt actgtttatg taagcagaca gttttattgt tcatgatgat    6600
atatttttat cttgtgcaat gtaacatcag agattttgag acacaacgtg ctttcccccc    6660
ccccccccat gacattaacc tataaaaata ggcgtatcac gaggcccttt cgtctcgcgc    6720
gtttcggtga tgacggtgaa aacctctgac acatgcagct cccggagacg gtcacagctt    6780
gtctgtaagc ggatgccggg agcagacaag cccgtcaggg cgcgtcagcg ggtgttggcg    6840
ggtgtcgggg ctggcttaac tatgcggcat cagagcagat tgtactgaga gtgcaccata    6900
```

-continued

```
aaattgtaaa cgttaatatt ttgttaaaat tcgcgttaaa tttttgttaa atcagctcat       6960
tttttaacca atagaccgaa atcggcaaaa tcccttataa atcaaaagaa tagcccgaga       7020
tagagttgag tgttgttcca gtttggaaca agagtccact attaaagaac gtggactcca       7080
acgtcaaagg gcgaaaaacc gtctatcagg gcgatggccc accccgattt agagcttgac       7140
ggggaaagcc ggcgaacgtg gcgagaaagg aagggaagaa agcgaaagga gcgggcgcta       7200
aggcgctggc aagtgtagcg gtcacgctgc gcgtaaccac cacacccgcc gcgcttaatg       7260
cgccgctaca gggcgcgtac tatggttgct ttgacgtatg cggtgtgaaa taccgcacag       7320
atgcgtaagg agaaaatacc gcatcaggcg ccattcgcca ttcaggctgc gcaactgttg       7380
ggaagggcga tcggtgcggg cctcttcgct attacgccag ctggcgaaag ggggatgtgc       7440
tgcaaggcga ttaagttggg taacgccagg gttttcccag tcacgacgtt gtaaaacgac       7500
ggccagtgaa ttgtaatacg actcactata gggcgaattg gggatcgatc cactagttct       7560
agagcggccg ccacggcgat atcggatcca tatgacgtcg acgcgtctgc ag              7612
```